US011988674B2

(12) United States Patent
Kordus et al.

(10) Patent No.: US 11,988,674 B2
(45) Date of Patent: May 21, 2024

(54) METHODS FOR MEASURING GENE EXPRESSION LEVELS TO IDENTIFY VIABLE OOCYTES

(71) Applicant: UNIVERSITY OF SOUTH CAROLINA, Columbia, SC (US)

(72) Inventors: Richard Kordus, Simpsonville, SC (US); Holly Lavoie, Hopkins, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 1387 days.

(21) Appl. No.: 16/295,564

(22) Filed: Mar. 7, 2019

(65) Prior Publication Data

US 2020/0049716 A1    Feb. 13, 2020

Related U.S. Application Data

(60) Provisional application No. 62/715,345, filed on Aug. 7, 2018.

(51) Int. Cl.
*G01N 33/68* (2006.01)
*C12N 5/073* (2010.01)

(52) U.S. Cl.
CPC ......... *G01N 33/689* (2013.01); *C12N 5/0604* (2013.01); *G01N 2800/367* (2013.01); *G01N 2800/368* (2013.01)

(58) Field of Classification Search
None
See application file for complete search history.

(56) References Cited

U.S. PATENT DOCUMENTS

| | | | |
|---|---|---|---|
| 6,172,198 B1 | 1/2001 | Sinosich | |
| 8,541,245 B2 | 9/2013 | Roudebush | |
| 2011/0091920 A1 | 4/2011 | Oxvig et al. | |
| 2011/0111523 A1 | 5/2011 | Roudebush | |
| 2012/0164636 A1 | 6/2012 | Sirard et al. | |
| 2013/0034906 A1 | 2/2013 | Smith et al. | |
| 2013/0137590 A1 | 5/2013 | Wells et al. | |
| 2014/0011206 A1 | 1/2014 | Latham et al. | |

FOREIGN PATENT DOCUMENTS

| | | | | |
|---|---|---|---|---|
| CN | 103614334 | | 3/2014 | |
| CN | 104531612 | | 4/2015 | |
| EP | 2400303 | | 12/2011 | |
| WO | WO 2005/035732 | | 4/2005 | |
| WO | WO 2005/097978 | | 10/2005 | |
| WO | WO 2008/031226 | * | 3/2008 | ............... C12Q 1/68 |
| WO | WO 2012/109326 | * | 2/2012 | ............... C12Q 1/68 |
| WO | WO 2014/125129 | | 8/2014 | |

OTHER PUBLICATIONS

HSD3B1, MeSH Database, downloaded on Aug. 24, 2022 from https://www.ncbi.nlm.nih.gov/mesh/ on Aug. 24, 2022 (Year: 2022).*
HSD3B2, MeSH Database, downloaded from https://www.ncbi.nlm.nih.gov/mesh/ on Aug. 24, 2022 (Year: 2022).*
Kordus et al., J Assist Reprod Genet (2019) 36:1457-1469 (Year: 2019).*
Balaban et al., Fertil Steril. 2001;75:514-8 (Year: 2001).*
Harvey J. Stern, J. Clin. Med. 2014, 3, 280-309 (Year: 2014).*
Adriaenssens, et al. "Cumulus cell gene expression is associated with oocyte developmental quality and influenced by patient and treatment characteristics" *Hum Reprod* 25(5) (2010) pp. 1259-1270.
Al-Edani, et al. "Female aging alters expression of human cumulus cells genes that are essential for oocyte quality" *Biomed Res Int* 2014:964614 (2014) pp. 1-11.
Allegra, et al. "The gene expression profile of cumulus cells reveals altered pathways in patients with endometriosis" *J Assist Reprod Genet* 31 (2014) pp. 1277-1285.
Assidi, et al. "Biomarkers of human oocyte developmental competence expressed in cumulus cells before ICSI: a preliminary study" *J Assist Reprod Genet* 28 (2011) pp. 173-188.
Assidi, et al. "Identification of potential markers of oocyte competence expressed in bovine cumulus cells matured with follicle-stimulating hormone and/or phorbol myristate acetate in vitro" *Biol Reprod* 79 (2008) pp. 209-222.
Assou, et al. "Comparative gene expression profiling in human cumulus cells according to ovarian gonadotropin treatments" *Biomed Res Int* 2013:354582 (2013) pp. 1-14.
Assou, et al. "A non-invasive test for assessing embryo potential by gene expression profiles of human cumulus cells: a proof of concept study" *Mol. Hum. Reprod.* 14(12) (2008) pp. 711-719.
Baerwald, et al. "Synchronization of ovarian stimulation with follicle wave emergence in patients undergoing in vitro fertilization with a prior suboptimal response: a randomized, controlled trial" *Fertil Steril* 98 (2012) pp. 881-887.
Barcelos, et al. "Down-regulation of the CYP19A1 gene in cumulus cells of infertile women with endometriosis" *Reprod Biomed Online* 30 (2015) pp. 532-541.
Bates, et al. "Fitting linear mixed-effects models using lme4" *J Stat Softw* 67 (2015) pp. 1-51.

(Continued)

Primary Examiner — Christina M Borgeest
(74) Attorney, Agent, or Firm — DORITY & MANNING, P.A

(57) ABSTRACT

The present invention is directed to non-invasive methods for performing selection of ova, otherwise referred to as oocytes, and/or embryos produced from fertilized oocytes. In an embodiment, performing the selection can include comparing the expression level of a gene in cumulus cell masses harvested from at least two oocytes or at least two embryos, the embryos formed by fertilizing the oocyte. In another embodiment, performing the selection can include comparing the expression level of a gene in a cumulus cell mass harvested from an oocyte or an embryo to a population value. By comparing the expression level of a gene (e.g., using either mRNA expression or protein expression) the embodiments and methods disclosed can provide advantages in selecting an egg for fertilization or an embryo for implantation, such as increasing the chances of successful fertilization and/or live birth. Aspects of this disclosure can provide methods for improving the outcome of in vitro fertilization (IVF) protocols through non-invasive genetic testing using a set of markers for determining or predicting the embryo ploidy status and live birth outcome.

16 Claims, 24 Drawing Sheets

(56) References Cited

OTHER PUBLICATIONS

Blaha, et al. "Gene expression analysis of pig cumulus-oocyte complexes stimulated in vitro with follicle stimulating hormone or epidermal growth factor-like peptides" *Reprod Biol Endocrinol* 13(113) (2015) pp. 1-17.

Borup, et al. "Competence Classification of Cumulus and Granulosa Cell Transcriptome in Embryos Matched by Morphology and Female Age" *PLoS One* 11:e0153562 (2016) pp. 1-19.

Brannian, et al. "Differential gene expression in human granulosa cells from recombinant FSH versus human menopausal gonadotropin ovarian stimulation protocols" *Reprod Biol Endocrinol* 8(25) (2010) pp. 1-6.

Burnik-Papler, et al. "No specific gene expression signature in human granulosa and cumulus cells for prediction of oocyte fertilisation and embryo implantation" *PLoS One* 10:e0115865 (2015) pp. 1-13.

Catteau-Jonard, et al. "Anti-Mullerian hormone, its receptor, FSH receptor, and androgen receptor genes are overexpressed by granulosa cells from stimulated follicles in women with polycystic ovary syndrome" *J Clin Endocrinol Metab* 93 (2008) pp. 4456-4461.

Chang, et al. "Outcomes of in vitro fertilization with preimplantation genetic diagnosis: an analysis of the United States Assisted Reproductive Technology Surveillance Data 2011-2012" *Fertil Steril* 105 (2016) pp. 394-400.

Chen, et al. "Can comprehensive chromosome screening technology improve IVF/ICSI outcomes? A meta-analysis" *PLoS One* 10:e0140779 (2015) pp. 1-21.

Christenson, et al. "Research resource: preovulatory LH surge effects on follicular theca and granulosa transcriptomes" *Mol Endocrinol* 27 (2013) pp. 1153-1171.

Conley, et al. "Mammalian aromatases" *Reproduction* 121 (2001) pp. 685-695.

Conover, et al. "Pregnancy-associated plasma protein-a is the insulin-like growth factor binding protein-4 protease secreted by human ovarian granulosa cells and is a marker of dominant follicle selection and the corpus luteum" *Endocrinology* 142(5) (2001) p. 2155.

Conover, et al. "Evidence that the insulin-like growth factor binding protein-4 protease in human ovarian follicular fluid is pregnancy associated plasma protein-A" *J Clin Endocrinol Metab* 84 (1999) pp. 4742-4745.

Dumesic, et al. "Oocyte environment: follicular fluid and cumulus cells are critical for oocyte health" *Fertil Steril* 103(2) (2015) pp. 303-316.

Egea, et al. "OMICS: Current and future perspectives in reproductive medicine and technology" *J Hum Reprod Sci* 7 (2014) pp. 73-92.

Ekart, et al. "Ranking and selection of MII oocytes in human ICSI cycles using gene expression levels from associated cumulus cells" *Hum Reprod* 28(11) (2013) pp. 2930-2942.

Eppig, et al. "Mammalian oocyte growth and development in vitro" *Mol Reprod Dev* 44 (1996) pp. 260-273.

Esmaeili, et al. "The tumor suppressor ING1b is a novel corepressor for the androgen receptor and induces cellular senescence in prostate cancer cells" *J Mol Cell Biol* 8 (2016) pp. 207-220.

Esmaeili, et al. "A novel crosstalk between the tumor suppressors ING1 and ING2 regulates androgen receptor signaling" *J Mol Med* 94 (2016) pp. 1167-1179.

Feuerstein, et al. "Gene expression in human cumulus cells: one approach to oocyte competence" Hum Reprod 22(12) (2007) pp. 3069-3077.

Firth, et al. "Cellular actions of the insulin-like growth factor binding proteins" *Endocr Rev* 23(6) (2002) pp. 824-854.

Fragouli, et al. "Alteration of gene expression in human cumulus cells as a potential indicator of oocyte aneuploidy" *Hum Reprod* 27 (2012) pp. 2559-2568.

Fragouli, et al. "Transcriptomic profiling of human oocytes: association of meiotic aneuploidy and altered oocyte gene expression" *Mol Hum Reprod* 16 (2010) pp. 570-582.

Freimann, et al. "EGF-like factor epiregulin and amphiregulin expression is regulated by gonadotropins/cAMP in human ovarian follicular cells" *Biochem Biophys Res Commun* 324 (2004) pp. 829-834.

Gardner, et al. "Blastocyst score affects implantation and pregnancy outcome: towards a single blastocyst transfer" *Fertil Steril* 73(6) (2000) pp. 1155-1158.

Garkavtsev, et al. "The candidate tumour suppressor p33$^{ING1}$ cooperates with p53 in cell growth control" *Nature* 391 (1998) pp. 295-298.

Gatta, et al. "Gene expression profiles of cumulus cells obtained from women treated with recombinant human luteinizing hormone + recombinant human follicle-stimulating hormone or highly purified human menopausal gonadotropin versus recombinant human follicle-stimulating hormone alone" *Fertil Steril* 99 (2013) pp. 2000-2008.

Gilchrist, et al. "Oocyte-secreted factors: regulators of cumulus cell function and oocyte quality" *Hum Reprod Update* 14(2) (2008) pp. 159-177.

Glister, et al. "Changes in expression of bone morphogenetic proteins (BMPs), their receptors and inhibin co-receptor betaglycan during bovine antral follicle development: inhibin can antagonize the suppressive effect of BMPs on thecal androgen production" *Reproduction* 140 (2010) pp. 699-712.

Gonzalez-Fernandez, et al. "Patients with endometriosis and patients with poor ovarian reserve have abnormal follicle-stimulating hormone receptor signaling pathways" *Fertil Steril* 95(7) (2011) pp. 2373-2378.

Green, et al. "Cumulus cell transcriptome profiling is not predictive of live birth after in vitro fertilization: A paired analysis of euploid sibling blastocysts" *Fertil Steril* 109 (2018) pp. 460-466.

Greenseid, et al. "Differential granulosa cell gene expression in young women with diminished ovarian reserve" *Reprod Sci* 18 (2011) pp. 892-899.

Grondahl, et al. "Differences in gene expression of granulosa cells from women undergoing controlled ovarian hyperstimulation with either recombinant follicle-stimulating hormone or highly purified human menopausal gonadotropin" *Fertil Steril* 91 (2009) pp. 1820-1830.

Guzman, et al. "Human antral follicles <6 mm: a comparison between in vivo maturation and in vitro maturation in non-hCG primed cycles using cumulus cell gene expression" *Mol Hum Reprod* 19(1) (2013) pp. 7-16.

Hamel, et al. "Identification of differentially expressed markers in human follicular cells associated with competent oocytes" *Hum Reprod* 23(5) (2008) pp. 1118-1127.

Haouzi, et al. "LH/hCGR gene expression in human cumulus cells is linked to the expression of the extracellular matrix modifying gene TNFAIP6 and to serum estradiol levels on day of hCG administration" *Hum Reprod* 24 (2009) pp. 2868-2878.

Hayashi, et al. "Differential genome-wide gene expression profiling of bovine largest and second-largest follicles: Identification of genes associated with growth of dominant follicles" *Reprod Biol Endocrinol* 8(1): 11 (2010) pp. 1-14.

He, et al. "Expression profiling of human keratinocyte response to ultraviolet A: implications in apoptosis" *J Invest Dermatol* 122(2) (2004) pp. 533-543.

Hothorn, et al. "Simultaneous inference in general parametric models" *Biom J* 50 (2008) pp. 346-363.

Hourvitz, et al. "Pregnancy-associated plasma protein-A gene expression in human ovaries is restricted to healthy follicles and corpora lutea" *J Clin Endocrinol Metab* 85 (2000) pp. 4916-4920.

Huang, et al. "Altered amphiregulin expression induced by diverse luteinizing hormone receptor reactivity in granulosa cells affects IVF outcomes" *Reprod Biomed Online* 30 (2015) pp. 593-601.

Hurwitz, et al. "Reproductive aging is associated with altered gene expression in human luteinized granulosa cells" *Reprod Sci* 17 (2010) pp. 56-67.

Iager, et al. "Identification of a novel gene set in human cumulus cells predictive of an oocyte's pregnancy potential" *Fertil Steril* 99 (2013) pp. 745-752.

(56) References Cited

OTHER PUBLICATIONS

Jindal, et al. "Impaired gremlin 1 (GREM1) expression in cumulus cells in young women with diminished ovarian reserve (DOR)" *J Assist Reprod Genet* 29 (2012) pp. 159-162.

Kedem, et al. "Anti Mullerian Hormone (AMH) level and expression in mural and cumulus cells in relation to age" *J Ovarian Res* 7:113 (2014) pp. 1-5.

Kirkegaard, et al. "Choosing the best embryo by time lapse versus standard morphology" *Fertil Steril* 103 (2015) pp. 323-332.

Kordus, et al. "Granulosa cell biomarkers to predict pregnancy in ART: pieces to solve the puzzle" *Reproduction* 153 (2017) pp. R69-R83.

Kristensen, et al. "Hallmarks of human small antral follicle development: implications for regulation of ovarian steroidogenesis and selection of the dominant follicle" *Frontiers in Endocrinology* 8:376 (2017) pp. 1-10.

Kushnir, et al. "Effectiveness of in vitro fertilization with preimplantation genetic screening: A reanalysis of United States assisted reproductive technology data 2011-2012" *Fertil Steril* 106 (2016) pp. 75-79.

Lan, et al. "Functional microarray analysis of differentially expressed genes in granulosa cells from women with polycystic ovary syndrome related to MAPK/ERK signaling" *Sci Rep* 5:14994 (2015) pp. 1-10.

Laursen, et al. "Pregnancy-associated plasma protein-A (PAPP-A) cleaves insulin-like growth factor binding protein (IGFBP)-5 independent of IGF: implications for the mechanism of IGFBP-4 proteolysis by PAPP-A" *FEBS Lett* 504 (2001) pp. 36-40.

Lee, et al. "Association of creatin kinase B and peroxiredoxin 2 expression with age and embryo quality in cumulus cells" *J Assist Reprod Genet* 27 (2010) pp. 629-639.

Lemmen, et al. "The total pregnancy potential per oocyte aspiration after assisted reproduction-in how many cycles are biologically competent oocytes available?" *J Assist Reprod Genet* 33 (2016) pp. 849-854.

Mackenzie, et al. "Depot-specific steroidogenic gene transcription in human adipose tissue" *Clin Endocrinol* 69(6) (2008) pp. 848-854.

Maman, et al. "High expression of luteinizing hormone receptors messenger RNA by human cumulus granulosa cells is in correlation with decreased fertilization" *Fertil Steril* 97 (2012) pp. 592-598.

Matzuk, et al. "Intercellular communication in the mammalian ovary: oocytes carry the conversation" *Science* 296 (2002) pp. 2178-2180.

May-Panloup, et al. "Molecular characterization of corona radiata cells from patients with diminished ovarian reserve using microarray and microfluidic-based gene expression profiling" *Hum Reprod* 27 (2012) pp. 829-843.

Mazerbourg, et al. "Pregnancy-associated plasma protein-A (PAPP-A) in ovine, bovine, porcine, and equine ovarian follicles: involvement in IGF binding protein-4 proteolytic degradation and mRNA expression during follicular development" *Endocrinology* 142 (2001) pp. 5243-5253.

Mcreynolds, et al. "Impact of maternal aging on the molecular signature of human cumulus cells" *Fertil Steril* 98 (2012) pp. 1574-1580.

Meng, et al. "Downregulated expression of peroxiredoxin 4 in granulosa cells from polycystic ovary syndrome" *PLoS One* 8:e76460 (2013) pp. 1-6.

Mescher, A. "Janqueira's Basic Histology: Text and Atlas" *McGraw-Hill Medical* (12th Edition) 2010.

Nel-Themaat, et al. "A review of the promises and pitfalls of oocyte and embryo metabolomics" *Placenta* 32 (2011) pp. S257-S263.

Nelson-Degrave, et al. "Alterations in mitogen-activated protein kinase kinase and extracellular regulated kinase signaling in theca cells contribute to excessive androgen production in polycystic ovary syndrome" *Mol Endocrinol* 19 (2005) pp. 379-390.

Nelson-Degrave, et al. "Valproate potentiates androgen biosynthesis in human ovarian theca cells" *Endocrinology* 145(2) (2004) pp. 799-808.

Nivet, et al. "Changes in granulosa cells' gene expression associated with increased oocyte competence in bovine" *Reproduction* 145 (2013) pp. 555-565.

Papamentzelopoulou, et al. "LH receptor gene expression in cumulus cells in women entering an ART program" *J Assist Reprod Genet* 29 (2012) pp. 409-416.

Park, et al. "EGF-like growth factors as mediators of LH action in the ovulatory follicle" *Science* 303 (2004) pp. 682-684.

Parks, et al. "Corona cell RNA sequencing from individual oocytes revealed transcripts and pathways linked to euploid oocyte competence and live birth" *Reprod BioMed Online* 32 (2016) pp. 518-526.

Patrizio, et al. "From oocyte to baby: a clinical evaluation of the biological efficiency of in vitro fertilization" *Fertil Steril* 91 (2009) pp. 1061-1066.

Rabinowitz, et al. "Origins and rates of aneuploidy in human blastomeres" *Fertil Steril* 97 (2012) pp. 395-401.

Saini, et al. "Developmental competence of different quality bovine oocytes retrieved through ovum pick-up following in vitro maturation and fertilization" *Animal* 9(12) (2015) pp. 1979-1985.

Schmidt, et al. "Differential expression of inflammation-related genes in the ovarian stroma and granulosa cells of PCOS women" *Mol Hum Reprod* 20 (2014) pp. 49-58.

Schoolcraft, et al. "Clinical application of comprehensive chromosomal screening at the blastocyst stage" *Fertil Steril* 94 (2010) pp. 1700-1706.

Scott, et al. "Blastocyst biopsy with comprehensive chromosome screening and fresh embryo transfer significantly increases in vitro fertilization implantation and delivery rates: a randomized controlled trial" *Fertil Steril* 100 (2013) pp. 697-703.

Seder, et al. "Upregulated INHBA expression may promote cell proliferation and is associated with poor survival in lung adenocarcinoma" *Neoplasia* 11(4) (2009) pp. 388-396.

Simard, et al. "Molecular biology of the 3β-hydroxysteroid dehydrogenase/$\Delta^5$-$\Delta^4$ isomerase gene family" *Endocr Rev* 26 (2005) pp. 525-582.

Sisco, et al. "Isolation of genes differentially expressed in dominant and subordinate bovine follicles" *Endocrinology* 144 (2003) pp. 3904-3913.

Tallen, et al. "The inhibitor of growth 1 (ING1) proteins suppress angiogenesis and differentially regulate angiopoietin expression in glioblastoma cells" *Oncol Res* 18 (2009) pp. 95-105. (Abstract only).

Tanghe, et al. "Minireview: Functions of the cumulus oophorus during oocyte maturation, ovulation, and fertilization" *Mol Reprod Dev* 61 (2002) pp. 414-424.

Tsutsumi, et al. "Inhibitory effects of cholesterol sulfate on progesterone production in human granulosa-like tumor cell line, KGN" *Endocr J* 55(3) (2008) pp. 575-581.

Uyar, et al. "Metabolomic assessment of embryo viability" *Semin Reprod Med* 32 (2014) pp. 141-152.

Vigone, et al. "Transcriptome based identification of mouse cumulus cell markers that predict the developmental competence of their enclosed antral oocytes" *BMC Genomics* 14:380 (2013) pp. 1-7.

Wagner, et al. "Regulation of pregnancy-associated plasma protein A2 (PAPPA2) in a human placental trophoblast cell line (BeWo)" *Reprod Biol Endocrinol* 9:48 (2011) pp. 1-7.

Walker, et al. "Insulin-like growth factor binding proteins IGFBP3, IGFBP4, and IGFBP5 predict endocrine responsiveness in patients with ovarian cancer" *Clin Cancer Res* 13(5) (2007) pp. 1438-1444.

Wang, et al. "Connexin expression and gap junctional coupling in human cumulus cells: Contribution to embryo quality" *J Cell Mol Med* 13(5) (2009) pp. 972-984.

Wang, et al. "IGFs and IGF-binding proteins in the regulation of human ovarian and endometrial function" *Journal of Endocrinology* 161 (1999) pp. 1-13.

Wathlet, et al. "Pregnancy prediction in single embryo transfer cycles after ICSI using QPCR: Validation in oocytes from the same cohort" *PLoS One* 8:e54226 (2013) pp. 1-10.

Wathlet, et al. "New candidate genes to predict pregnancy outcome in single embryo transfer cycles when using cumulus cell gene expression" *Fertil Steril* 98 (2012) pp. 432-439.

(56) References Cited

OTHER PUBLICATIONS

Wathlet, et al. "Cumulus cell gene expression predicts better cleavage-stage embryo or blastocyst development and pregnancy for ICSI patients" *Hum Reprod* 26 (2011) pp. 1035-1051.

Webb, et al. "Development of the dominant follicle: mechanisms of selection and maintenance of oocyte quality" *Soc Reprod Fertil Suppl* 64 (2007) pp. 141-163.

Wei, et al. "Change and significance of growth differentiation factor 9 and bone morphogenetic protein expression during oocyte maturation in polycystic ovary syndrome patients with ovarian stimulation" *Zhonghua Fu Chan Ke Za Zhi* 47 (2012) pp. 818-822. (Abstract only).

Yanaihara, et al. "Strong expression of steroid sulfatase in human cumulus cells in patients with endometriosis" *Fertil Steril* 84 (2005) pp. 464-467.

Yang, et al. "Selection of single blastocysts for fresh transfer via standard morphology assessment alone and with array CGH for good prognosis IVF patients: results from a randomized pilot study" *Mol Cytogenet* 5:24 (2012) pp. 1-8.

Yung, et al. "Progesterone antagonist, RU486, represses LHCGR expression and LH/hCG signaling in cultured luteinized human mural granulosa cells" *Gynecol Endocrinol* 30(1) (2014) pp. 42-47.

Zachariades, et al. "Expression of membrane and nuclear progesterone receptors in two human placental choriocarcinoma cell lines (JEG-3 and BeWo): Effects of syncytialization" *Int J Mol Med* 27(6) (2011) pp. 767-774.

Zhang, et al. "Number of biopsied trophectoderm cells is likely to affect the implantation potential of blastocysts with poor trophectoderm quality" *Fertil Steril* 105 (2016) pp. 1222-1227.

Zhang, et al. "Studies of gene expression in human cumulus cells indicate pentraxin 3 as a possible marker for oocyte quality" *Fertil Steril* 83(4) (2005) pp. 1169-1179.

\* cited by examiner

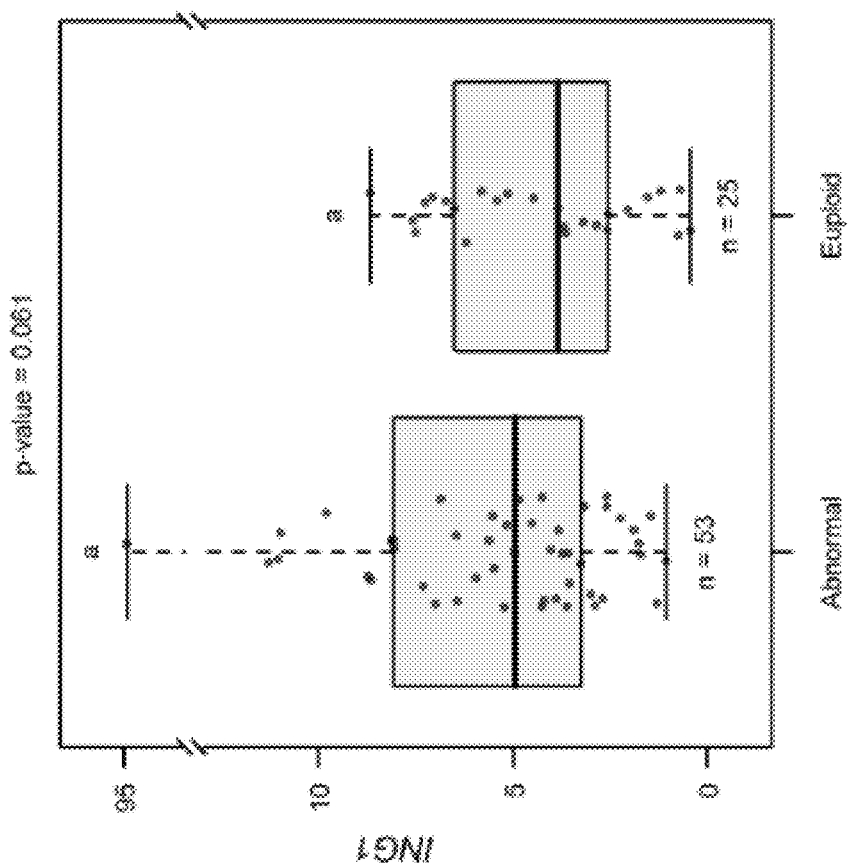
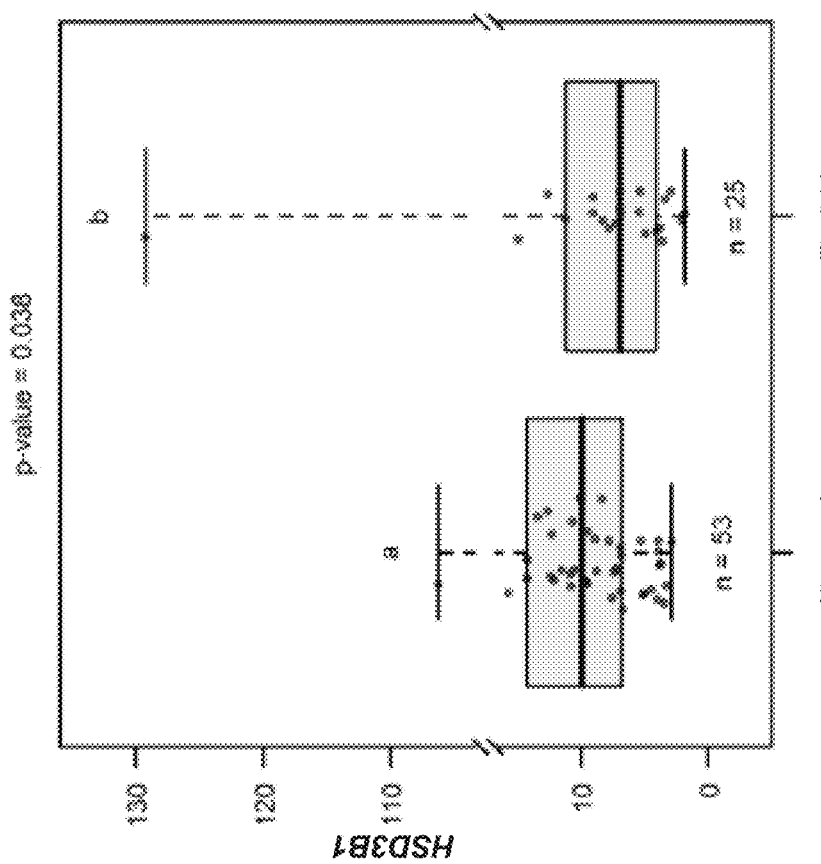
FIG. 2B
FIG. 2A

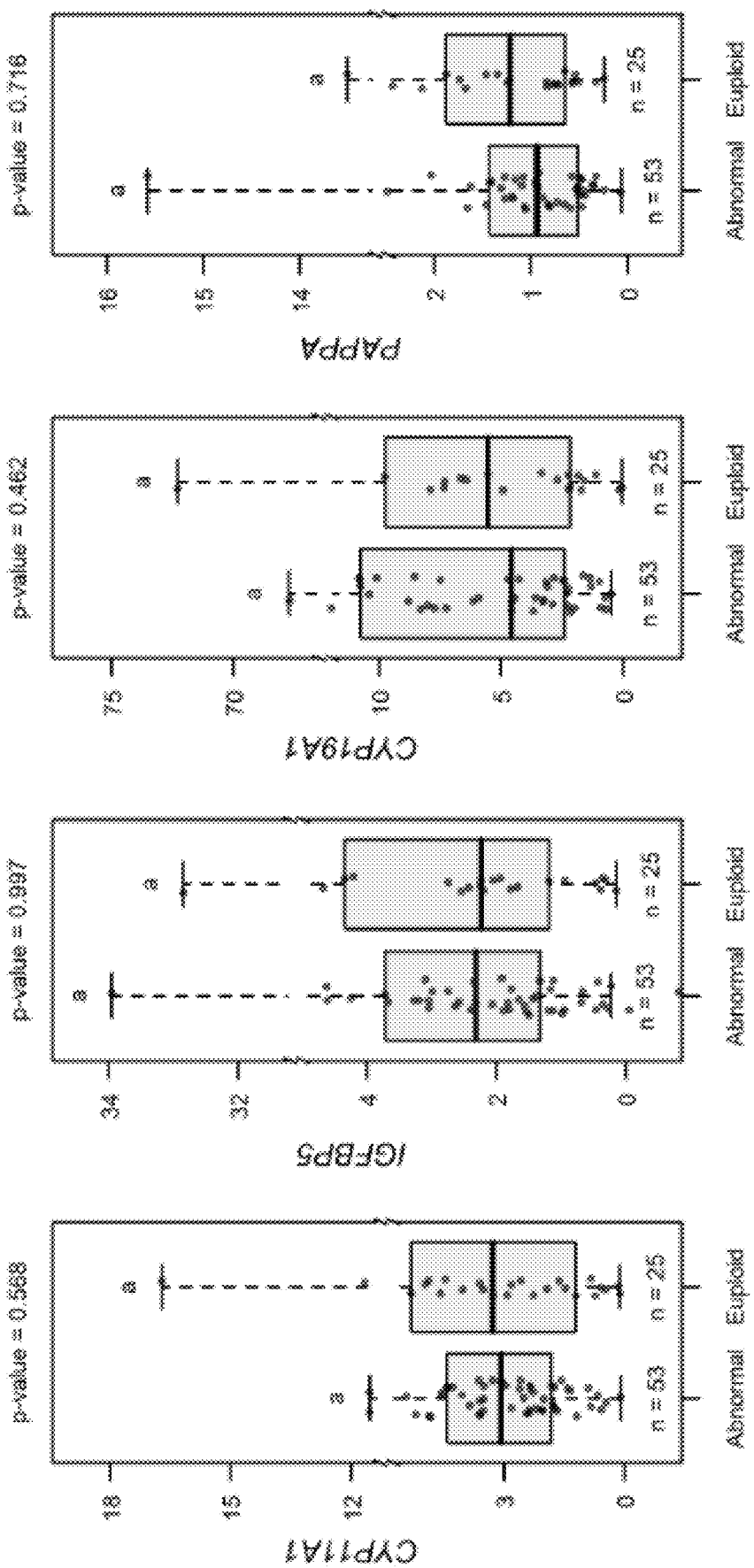

METHODS FOR MEASURING GENE EXPRESSION LEVELS TO IDENTIFY VIABLE OOCYTES

CROSS REFERENCE TO RELATED APPLICATION

This application claims filing benefit of U.S. Provisional Application Ser. No. 62/715,345 having a filing date of Aug. 7, 2018, which is incorporated herein by reference in its entirety.

BACKGROUND

Human in vitro fertilization (IVF) generates embryos that can be transferred to the uterus to achieve pregnancy and live birth. IVF is only successful in giving rise to live birth outcomes in about 50% of cycles. This is because it can be difficult to predict which of the generated embryos will result in live birth or which eggs to fertilize. A common method for embryo selection is morphological appearance; however, this metric can have several disadvantages. Assessing morphological appearance does not provide a quantitative measure that can be directly compared, and further can require an expert to perform the assessment. While pre-genetic testing for normal chromosomal number has been applied to select euploid embryos, there is still no guarantee that selecting a euploid embryo will result in uterine implantation or live birth. Additionally, most pre-genetic testing is considered invasive as it requires extracting material from the embryo or ovum.

For performing IVF procedures, multiple cumulus-oocyte complexes are normally collected from a donor. Cumulus cells surround the oocyte, which can be a mature or immature ovum, forming a cumulus-oocyte complex. The cumulus cells include the layer of cells that must be penetrated by spermatozoa for fertilization, and generally IVF procedures simply remove and discard the cumulus cells since they are not required to form the resulting embryo. Though associated with the egg, few studies have focused on the possible role of these cells, and the biomarkers they express, as possible indicators for fertilization and/or birth outcome.

There is a great need to develop predictive markers using non-invasive techniques that can improve the outcome of IVF procedures. Upwards of 60,000 IVF babies are born each year in the US and around 350,000 IVF babies born worldwide. To reach the US number, nearly 100,000 IVF cycles were performed (about 60% success rate). As such a method and/or system that can predict or improve the prediction of the viability of an embryo prior to implantation or egg prior to fertilization would be useful, especially if the method could be performed in a non-invasive manner.

SUMMARY OF THE INVENTION

The present invention is directed to non-invasive methods for performing selection of ova, otherwise referred to as oocytes, and/or embryos produced from fertilized oocytes. In an embodiment, performing the selection can include comparing the expression level of a gene in a cumulus cell mass harvested from at least two oocytes or at least two embryos, the embryos formed by fertilizing the oocyte. In another embodiment, performing the selection can include comparing the expression level of a gene in a cumulus cell mass harvested from an oocyte or an embryo to a population value. By comparing the expression level of a gene (e.g., using either mRNA expression or protein expression) the embodiments and methods disclosed can provide advantages in selecting an egg for fertilization or an embryo for implantation, such as increasing the chances of successful fertilization and/or live birth. Using the genetic information from the surrounding cumulus cell mass, a more informed decision can be made for recommending that the oocyte be fertilized, the embryo be implanted in a patient, and additional genetic testing be performed. Aspects of this disclosure can provide methods for improving the outcome of in vitro fertilization (IVF) protocols through the use of non-invasive genetic testing using a set of markers for determining or predicting the embryo ploidy status and live birth outcome. Further, the methods disclosed could provide for more cost-effective IVF procedures, since the number of embryos implanted, the number of ova fertilized, and the number of genetic tests performed can be reduced for patients undergoing the procedure.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIGS. 2A-2J illustrate example data for cumulus cells from oocytes having abnormal outcomes and those giving rise to euploid embryo populations.

Figure 1:
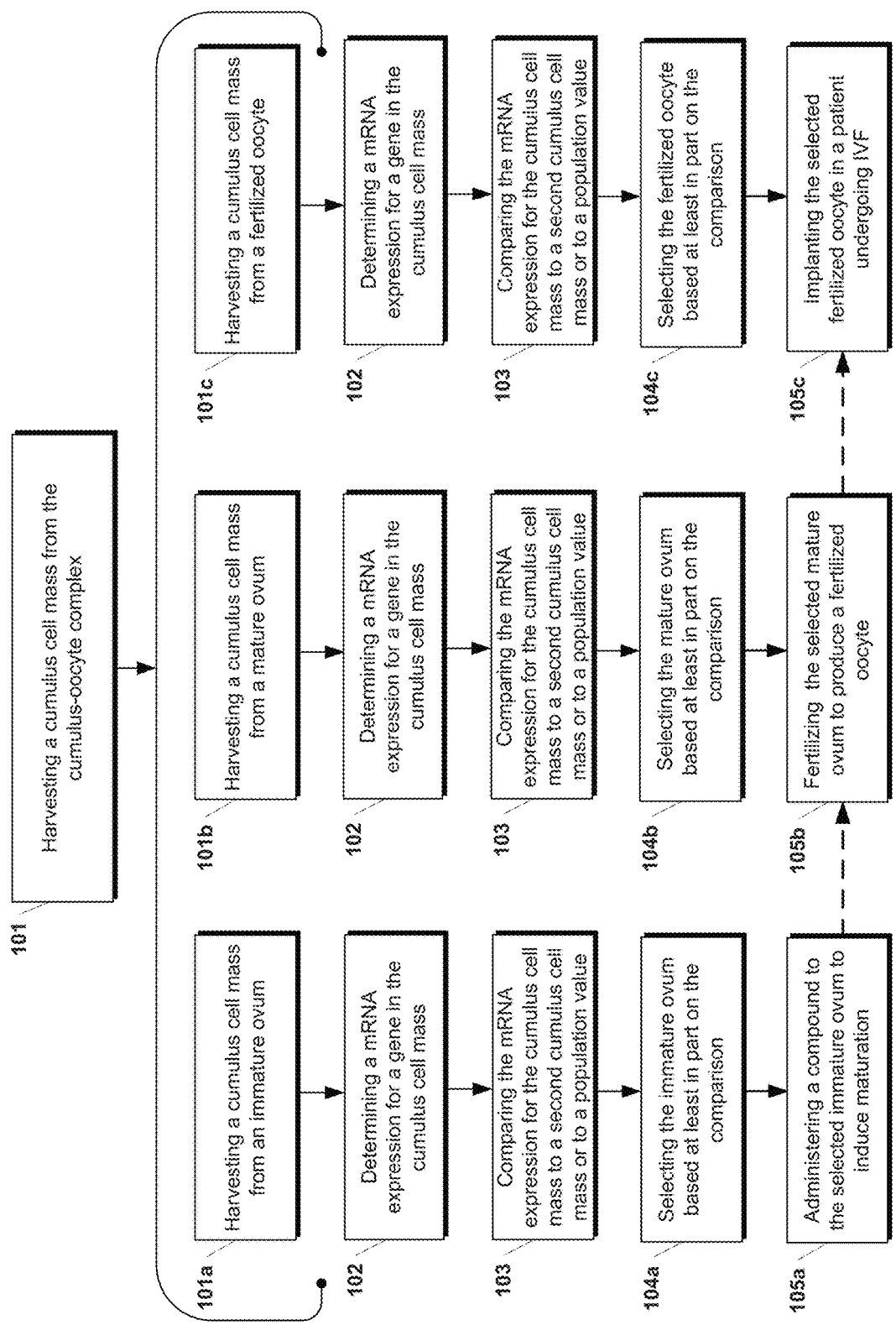
FIG. 1 illustrates a flow chart showing example embodiments of methods contemplated by the disclosure.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally speaking, the present invention is directed to non-invasive methods for performing selection of ova, otherwise referred to as oocytes. These methods can be applied to select an ovum at any stage of maturation or to select a fertilized embryo produced from the oocyte. The disclosed methods can provide advantages, such as increasing the chances of live birth, implantation, and/or fertilization, by measuring the expression levels of certain genes present in the cumulus cell mass that surrounds the oocytes. Using the genetic information from the cumulus cell mass, an informed decision can be made for recommending that the oocyte should be fertilized and/or whether additional genetic testing should be run. Thus, certain aspects of this disclosure are directed to improving the outcome of in vitro fertilization protocols by developing predicative markers for determining the embryo ploidy status and live birth outcome.

Embodiments of the disclosure can include methods for performing oocyte selection from a group of at least two oocytes (e.g., 2-100, 2-75, or 2-50). These methods can include harvesting a cumulus cell mass from each of at least two oocytes so that each harvested cumulus cell mass is associated with a corresponding oocyte from which the cumulus cell mass was harvested. The methods can further include determining a mRNA expression for a gene (e.g., pregnancy-associated plasma protein A also referred to as PAPPA) for each cumulus cell mass harvested from at least two oocytes. Alternatively or additionally, a protein expression may be determined to approximate and/or confirm genetic expression of the mRNA for each cumulus cell mass. The methods can further include comparing the mRNA expression for the gene in at least two cumulus cell masses harvested from different oocytes to determine the cumulus cell mass having a higher, a lower, or approximately the same mRNA expression. In certain implementations, the comparison may also determine whether the mRNA expression for the cumulus cell mass is statistically higher, lower, or the same compared to the mRNA expression determined for a second cumulus cell mass. Based at least in part on comparing the mRNA expression for at least two cumulus cell masses harvested from different oocytes, the methods can further include selecting the oocyte associated with one of at least two cumulus cell masses. Thus, example embodiments of the disclosure may be used to help patients make an informed decision for undergoing IVF or to inform doctors and/or fertility clinics to streamline or reduce the cost of IVF.

In an example implementation, at least two oocytes can be obtained from the same egg donor. In another example implementation, some or all of at least two oocytes can be obtained from different egg donors. Generally, the methods described herein can be applied to any group of oocytes, no matter the donor or donor characteristics. In certain implementations, using the same egg donor may provide an advantage by controlling for age, genetics, and/or other characteristics that can impact fertility or birth outcome.

As used herein, harvesting a cumulus cell mass from an oocyte can include, harvesting a cumulus cell mass from the cumulus-oocyte complex that is normally obtained in IVF procedures. In an embodiment, the cumulus-oocyte complex can include a mature ovum that can undergo fertilization without stimulation or further maturation. In another embodiment, the cumulus-oocyte complex can include an immature ovum that has not undergone meiosis or contains an abnormal number of chromosomes (aneuploidy). Harvesting a cumulus cell mass from an oocyte can also include harvesting a cumulus cell mass from a fertilized oocyte (also referred to as an embryo). In an embodiment, the fertilized oocyte can include one or more surrounding cumulus cells that may be used with the methods disclosed herein. Thus, for embodiments of the disclosure, harvesting cumulus cells from the oocyte can be performed at any stage of oocyte/egg maturity or at any stage of oocyte/egg fertilization (e.g., unfertilized or embryo).

Generally, the cumulus cell mass can include any number of cumulus cells such as 1-100, 1-1000, 1-10000, 1-100000, or greater than 100000. In certain implementations, it may be advantageous to harvest a greater number of cumulus cells to improve detection of gene expression or to produce a statistically significant measurement. However, these ranges are provided for illustration only and are not intended to limit the scope of the disclosure or the embodiments presented herein. As such, a cumulus cell, a cumulus cell mass, the cumulus cell, the cumulus cell mass, cumulus cell, and cumulus cells can be used interchangeably throughout the application to refer to one or more cumulus cells.

In an embodiment of the disclosure, determining the mRNA expression can include determining a quantitative expression such that the mRNA expression can be expressed as a numeric value. Non-limiting examples of techniques for quantifying mRNA expression include: quantitative real time Polymerase Chain Reaction (qRT-PCR), Western Blot assay, and enzyme-linked immunosorbent assay (ELISA). Techniques such as Western Blot and ELISA can be used to measure the amount of a specific protein by using an antibody capable of binding to the specific protein. In this manner, protein expression and/or mRNA expression could be employed as methods for quantifying mRNA expression.

In certain embodiments, comparing the mRNA expression for the gene can include categorizing or organizing the mRNA expression determined for the cumulus cell masses. In an embodiment, categorizing the mRNA expression can be based on a relative comparison using the mRNA expression obtained from at least two different cumulus cell masses. As an example, the mRNA expression obtained from a group of 3 cumulus cell masses could include the values (e.g., 0.2, 0.3, and 0.8) for a gene of interested. From these values a statistic may be calculated such as the minimum (e.g., 0.2), the maximum (e.g., 0.8), or the average (e.g., 0.43) to characterize how the mRNA expression determined for one of the cumulus cell masses compares to the group of cumulus cell masses. In some implementations, the statistic can also include a percentile, a median, a mode, a probability, or a combination of these statistics. In some implementations, the comparison can be binary such as determining whether a value (e.g., mRNA expression) is higher, lower, or equal to a second value.

In an embodiment, the method for selecting an oocyte from a group of at least two can also include making a decision based on the informed selection of an oocyte. An example decision can include fertilizing the selected oocyte for use in an in vitro fertilization procedure. Another example decision can include conducting genetic testing on the selected oocyte. An additional decision could include a recommendation (e.g., to proceed with fertilization using the selected oocyte, to not proceed with fertilization using the selected oocyte, to test a different group of oocytes, or to conduct a genetic test on the selected oocyte).

For embodiments of the disclosure, the gene can include one or a combination of the following: amphiregulin (AREG), cholesterol side-chain cleavage enzyme (CYP11A1), aromatase (CYP19A1), follicle-stimulating hormone receptor (FSHR), hydroxy-delta-5-steroid dehydrogenase, 3 beta- and steroid delta-isomerase 1 (HSD3B1), insulin-like growth factor-binding protein 5 (IGFBP5), inhibin beta A (INHBA), luteinizing hormone/choriogonadotropin receptor (LHCGR), progesterone receptor (PGR), progesterone receptor membrane component (PGRMC1), prostaglandin-endoperoxide synthase 2 (PTGS2), inhibitor of growth protein 1 (ING1), and Pappalysin 1 (PAPPA).

In an example embodiment, selecting the corresponding oocyte can include comparing the mRNA expression of AREG for at least two cumulus cell masses and selecting the corresponding oocyte associated with the cumulus cell mass having a lower mRNA expression of AREG based on a threshold or a statistic that can be determined using the mRNA expression. As an example, the threshold can be the minimum mRNA expression of AREG and selecting the corresponding oocyte can include selecting the oocyte associated with the cumulus cell mass having the minimum (i.e., lowest) mRNA expression of AREG. As another example, the threshold can be a percentile such as the lower quartile or the lower 10% and selecting the corresponding oocyte can include selecting any oocyte associated with a cumulus cell mass equal to or less than the threshold (e.g., having a mRNA expression of AREG in the lower 25% of values determined for the mRNA expression of AREG for each of at least two cumulus cell masses).

Additionally or alternatively, selecting the corresponding oocyte can include comparing the mRNA expression of HSD3B1 for at least two cumulus cell masses and selecting the corresponding oocyte associated with the cumulus cell mass having a lower mRNA expression of HSD3B1 based on a threshold or a statistic that can be determined using the mRNA expression. As an example, the threshold can be the minimum mRNA expression of HSD3B1 and selecting the corresponding oocyte can include selecting the oocyte associated with the cumulus cell mass having the minimum (i.e., lowest) mRNA expression of HSD3B. As another example, the threshold can be a percentile such as the lower quartile or the lower 10% and selecting the corresponding oocyte can include selecting any oocyte associated with a cumulus cell mass equal to or less than the threshold (e.g., having a mRNA expression of HSD3B1 in the lower 25% of values determined for the mRNA expression of HSD3B1 for each of at least two cumulus cell masses).

Additionally or alternatively, selecting the corresponding oocyte can include comparing the mRNA expression of LHCGR for at least two cumulus cell masses and selecting the corresponding oocyte associated with the cumulus cell mass having a higher mRNA expression of LHCGR based on a threshold or a statistic that can be determined using the mRNA expression. As an example, the threshold can be the maximum mRNA expression of LHCGR and selecting the corresponding oocyte can include selecting the oocyte associated with the cumulus cell mass having the maximum (i.e., highest) mRNA expression of LHCGR. As another example, the threshold can be a percentile such as the upper quartile or the upper 10% and selecting the corresponding oocyte can include selecting any oocyte associated with a cumulus cell mass equal to or greater than the threshold (e.g., having a mRNA expression of LHCGR in the upper 25% of values determined for the mRNA expression of LHCGR for each of at least two cumulus cell masses).

Additionally or alternatively, selecting the corresponding oocyte can include comparing the mRNA expression of PAPPA for at least two cumulus cell masses and selecting the corresponding oocyte associated with the cumulus cell mass having a higher mRNA expression of PAPPA based on a threshold or a statistic that can be determined using the mRNA expression. As an example, the threshold can be the maximum mRNA expression of PAPPA and selecting the corresponding oocyte can include selecting the oocyte associated with the cumulus cell mass having the maximum (i.e., highest) mRNA expression of PAPPA. As another example, the threshold can be a percentile such as the upper quartile or the upper 10% and selecting the corresponding oocyte can include selecting any oocyte associated with a cumulus cell mass equal to or greater than the threshold (e.g., having a mRNA expression of PAPPA in the upper 25% of values determined for the mRNA expression of PAPPA for each of at least two cumulus cell masses).

In some embodiments, selecting the corresponding oocyte can also include a probability that can be weighted in certain embodiments. For example, if selecting the corresponding oocyte is based in part on the associated cumulus cell mass having a lower mRNA expression of a gene, then a weighted probability can be applied to the values for the mRNA expression such that the cumulus cell mass having the lowest mRNA expression has the highest probability for selection (e.g., 80%). The probability for selecting the cumulus cell mass having the second lowest mRNA expression then can have a lower probability for selection (e.g., 75%). The probability for selecting the cumulus cell mass having the third lowest mRNA expression then can have an even lower probability for selection (e.g., 70%). These examples illustrate a linear decrease in probability based on the proximity to the threshold (e.g., the minimum mRNA expression). However, this does not restrict the types of probability models that can be applied to embodiments of the disclosure. For example, in some embodiments, the probability could be the same for all cumulus cell masses that meet the threshold for mRNA expression. In certain embodiments, the probability can include a linear gradient. In still other embodiments, the probability can include a logarithmic gradient.

Additionally, a probability or a weighted probability may be determined for embodiments where selecting the corresponding oocyte is based in part on the associated cumulus cell mass having a higher mRNA expression of a gene. As an example, a weighted probability can be applied to the values for the mRNA expression such that the cumulus cell mass having the highest mRNA expression has the highest probability for selection (e.g., 80%). The probability for selecting the cumulus cell mass having the second highest mRNA expression then can have a lower probability for selection (e.g., 75%). The probability for selecting the cumulus cell mass having the third highest mRNA expression then can have an even lower probability for selection (e.g., 70%). These examples illustrate a linear decrease in probability based on the proximity to the threshold (e.g., the maximum mRNA expression). However, this does not restrict the types of probability models that can be applied to embodiments of the disclosure. For example, in some embodiments, the probability could be the same for all cumulus cell masses that meet the threshold for mRNA expression. In certain embodiments, the probability can include a linear gradient. In still other embodiments, the probability can include a logarithmic gradient such that the probability for selection decreases exponentially based on proximity to the threshold.

Another example embodiment of the disclosure can include a method for selecting an oocyte for fertilization, the method including: harvesting a cumulus cell mass from an oocyte; determining an mRNA expression for a gene from the cumulus cell mass; comparing the mRNA expression for the gene to a population value; and selecting the oocyte for fertilization based at least in part on comparison to the population value. For this embodiment, it may or may not be necessary to directly compare the mRNA expression values between cumulus cell masses derived from at least two oocytes. In an exemplary embodiment, a population value can be determined from samples from a group of cumulus cell masses harvested from different oocytes. Based on the mRNA expression for the group of cumulus cell masses and the outcomes of the different oocytes (e.g., aneuploid, arrested, failed fert, immature, live birth, no pregnancy), a population value can be determined.

Figure 3A:
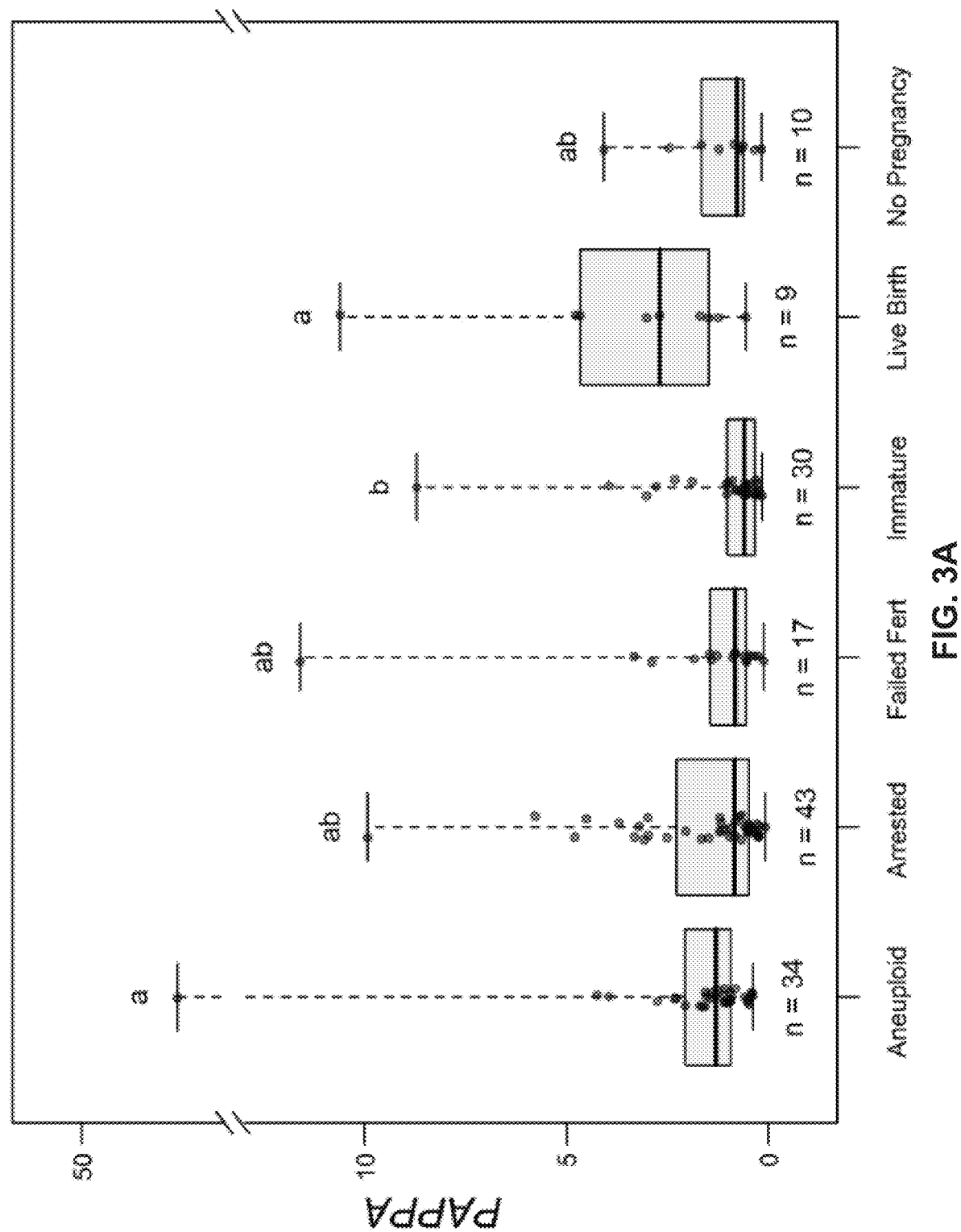
FIGS. 3A-3B illustrate example data displaying the following populations: oocytes giving rise to aneuploid embryos, arrested embryos, oocyte which failed fertilization (failed fert), immature oocytes, oocytes giving rise to euploid embryos with live birth, oocytes giving rise to euploid embryos with no pregnancy.

For example, referring now to FIG. 3A, the figure illustrates the mRNA expression for PAPPA in cumulus cell masses harvested from oocytes, and the outcome for the corresponding oocytes. Generally, the mRNA expression for PAPPA resulting in a live birth outcome is greater than the mRNA expression for PAPPA in other outcomes (the median mRNA expression is greater than the median mRNA expression for other outcomes). Thus, the population value for PAPPA can be determined based on the mRNA expression for cumulus cell masses harvested from oocytes having a live birth outcome (e.g., the median, lower quartile, or upper quartile). Alternatively, the population value for PAPPA can be determined based on the mRNA expression for cumulus cell masses harvested from oocytes not having a live birth outcome.

Figure 4A:
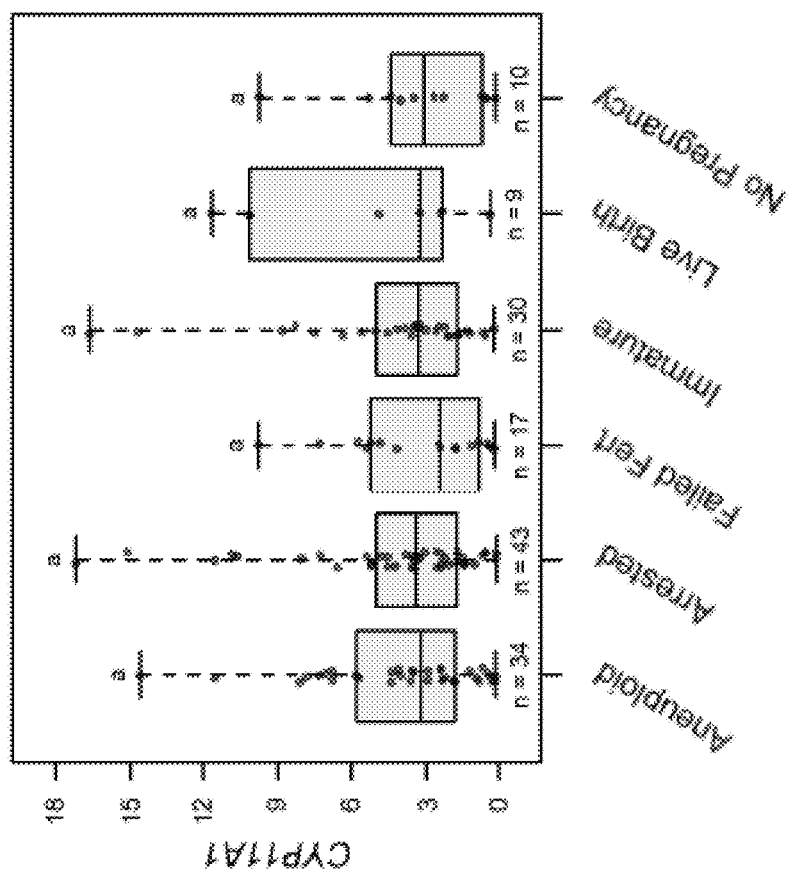
FIGS. 4A-4P further illustrate example data displaying the following populations: aneuploid, arrested, failed fert, immature, live birth, no pregnancy.
Figure 4B:
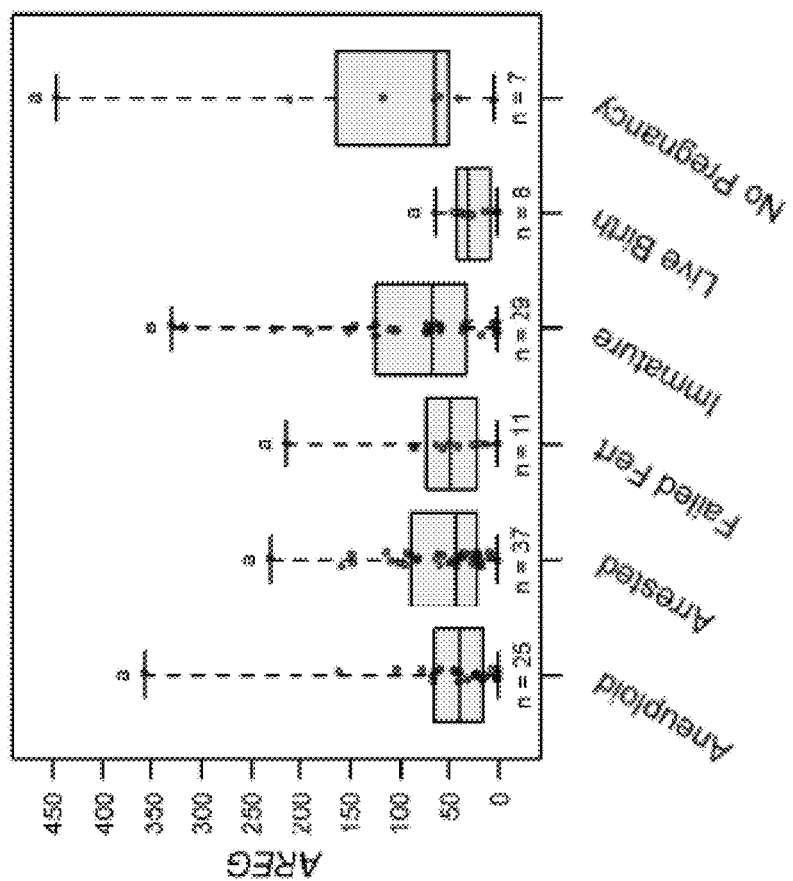
Figure 4C:
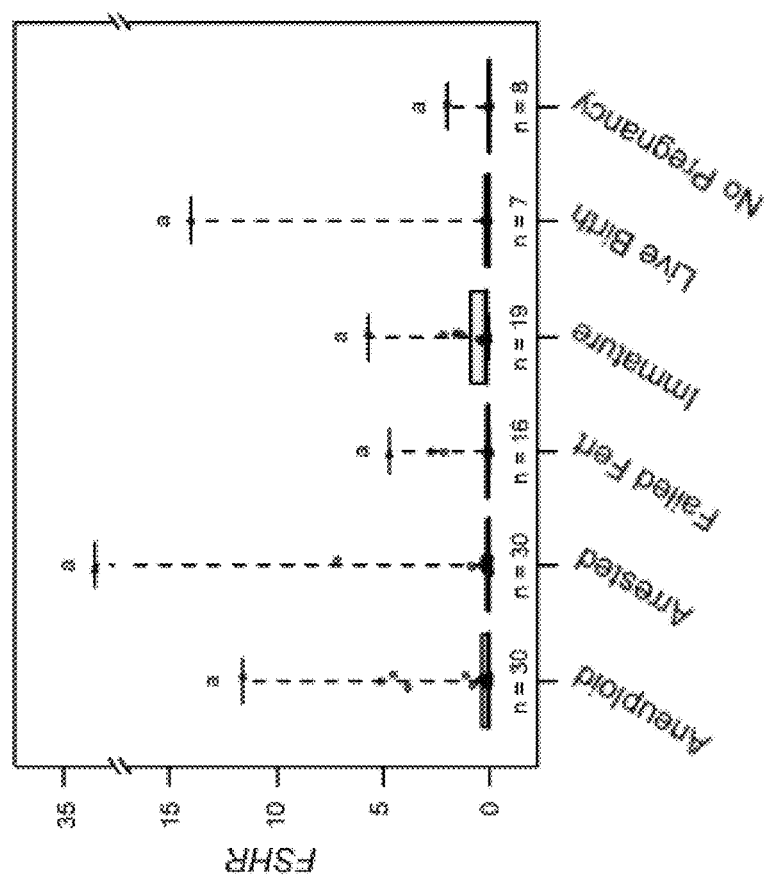
Figure 4D:
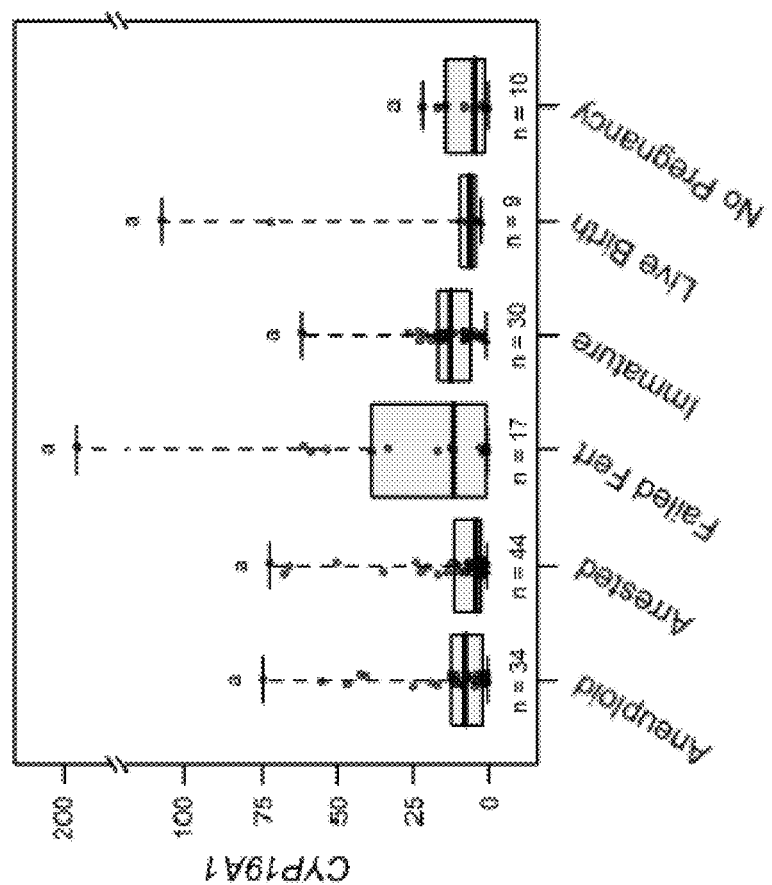
Figure 4F:
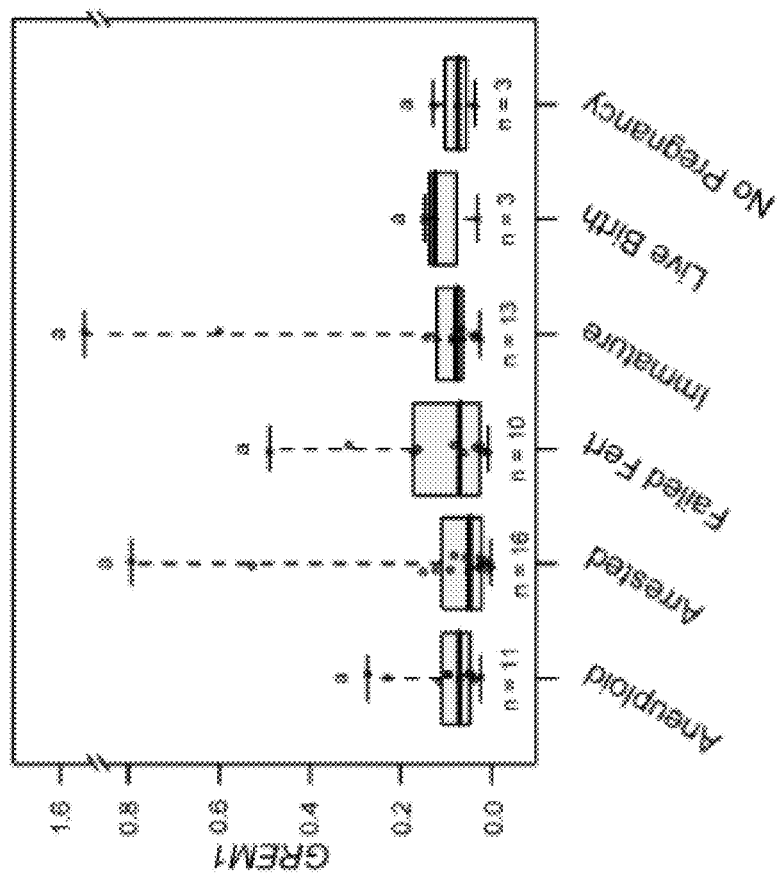
Figure 4E:
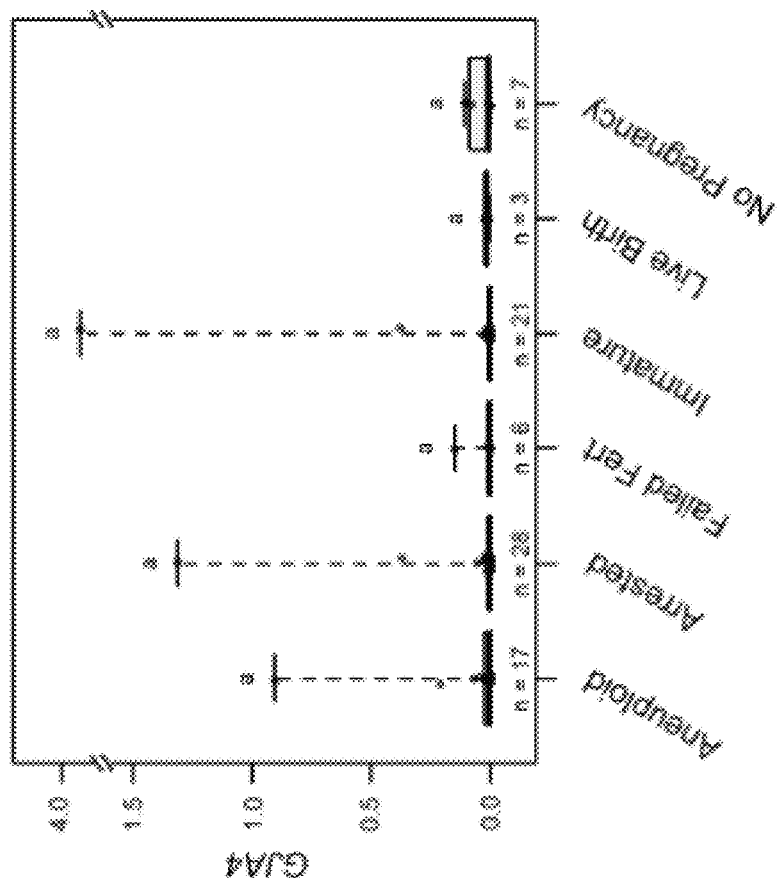
Figure 4H:
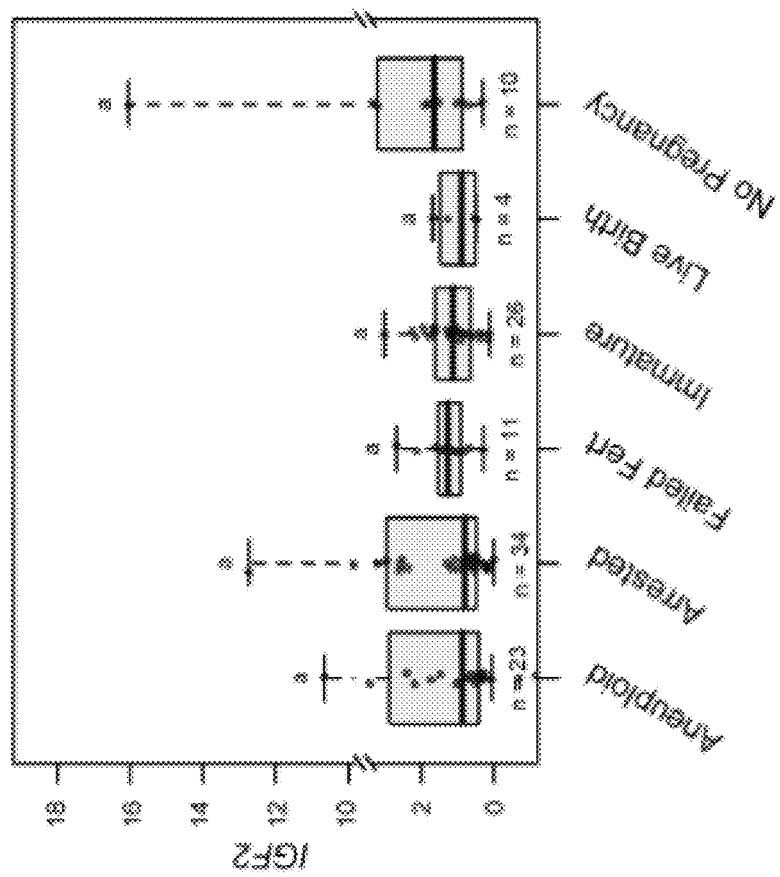
Figure 4G:
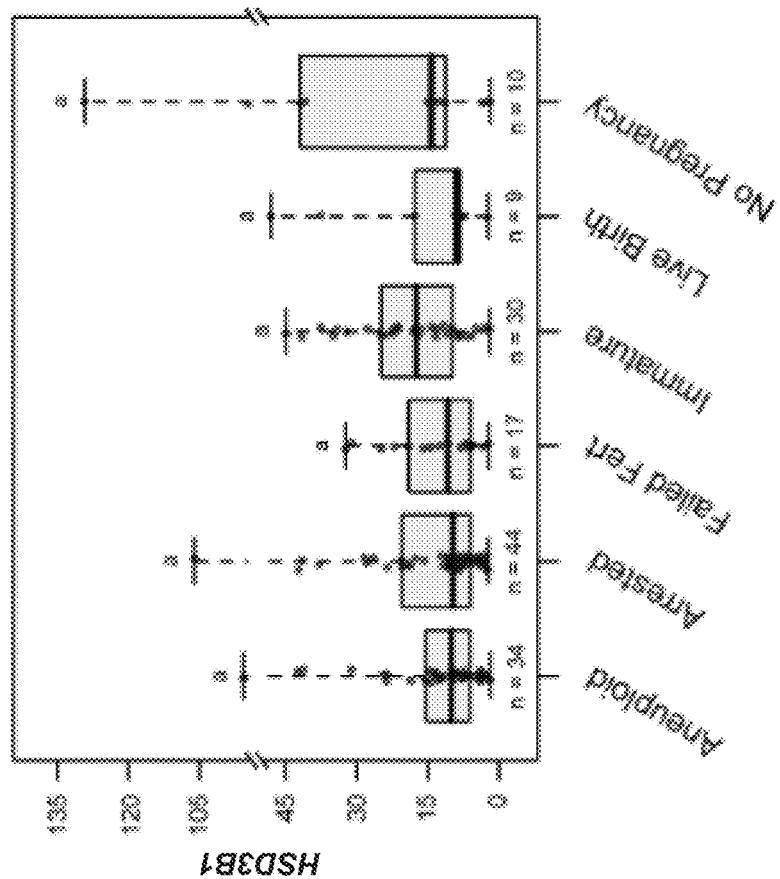
Figure 4J:
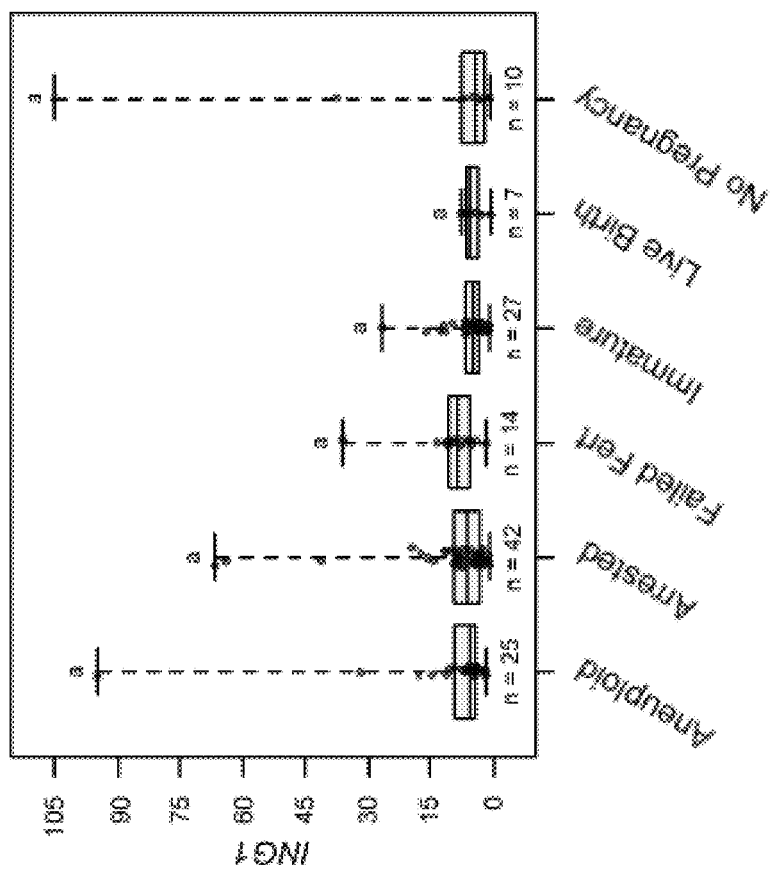
Figure 4I:
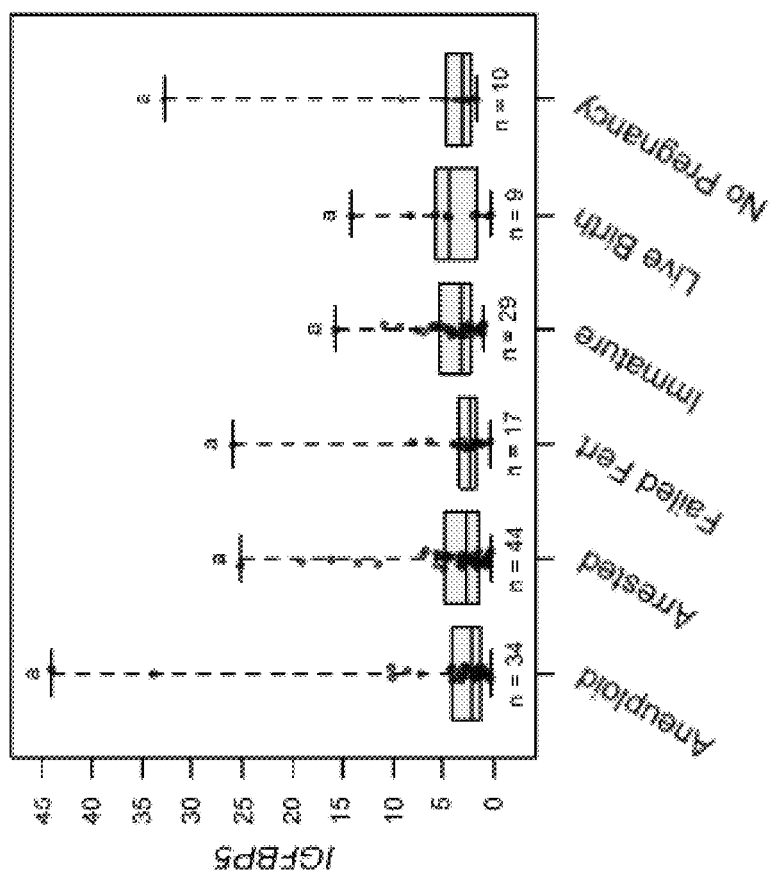
Figure 4L:
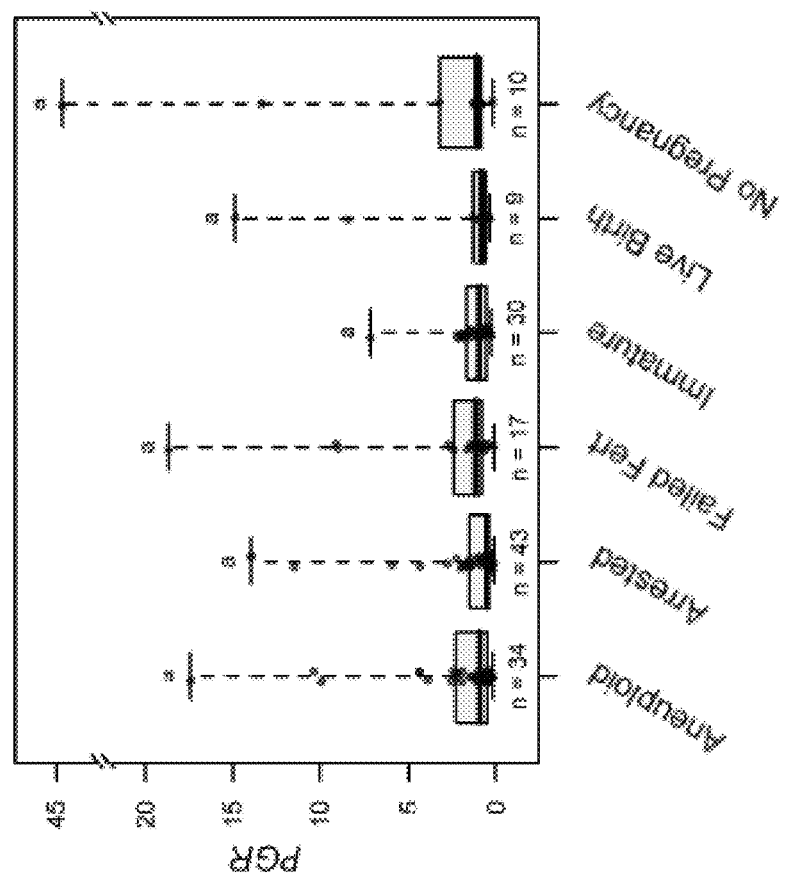
Figure 4K:
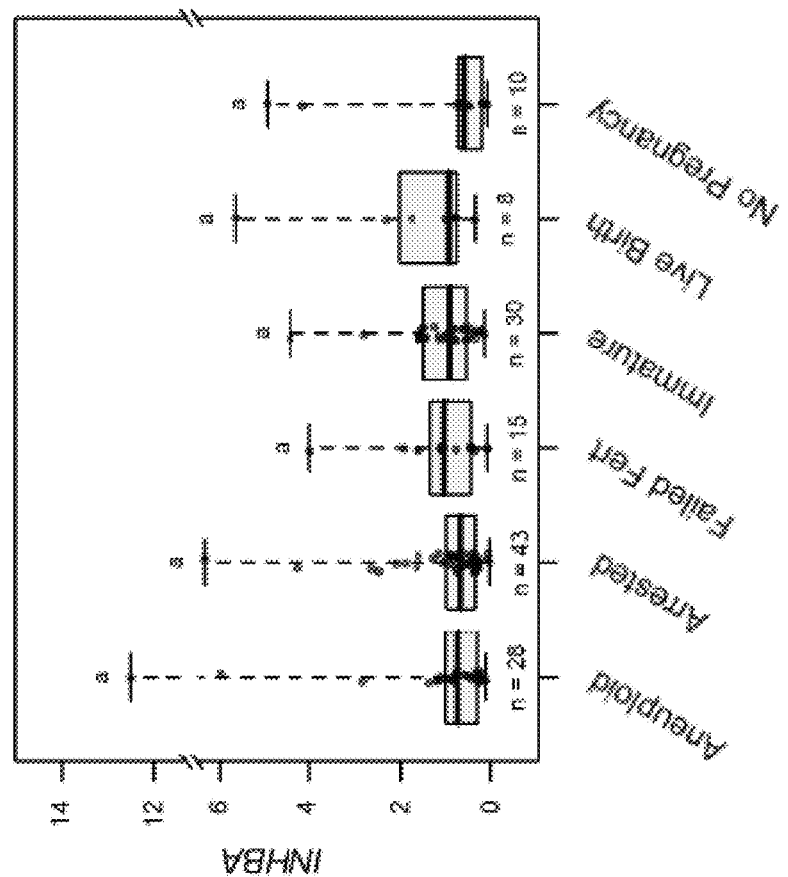
Figure 4N:
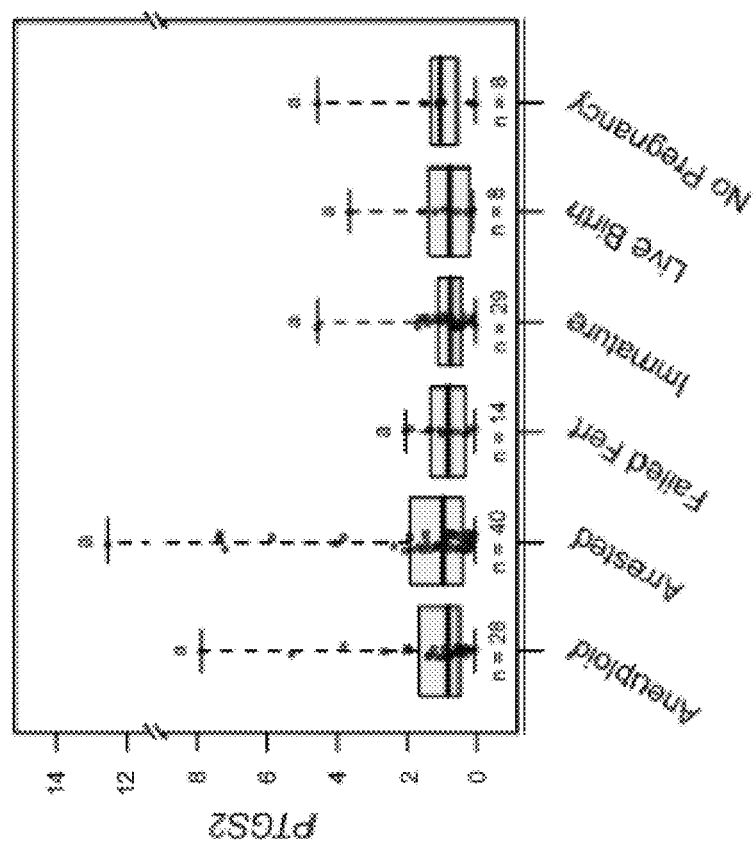
Figure 4M:
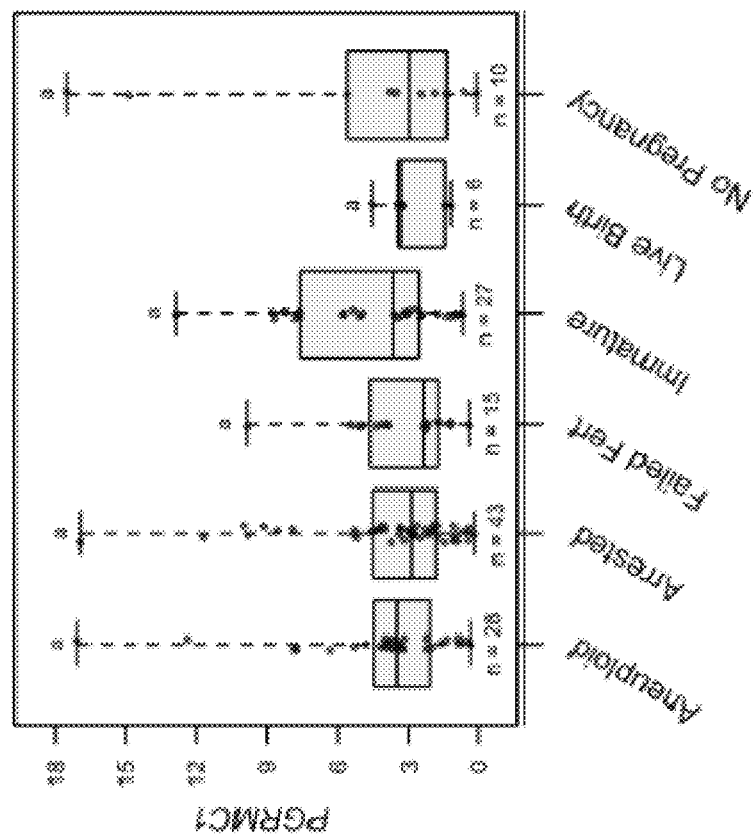
Figure 4P:
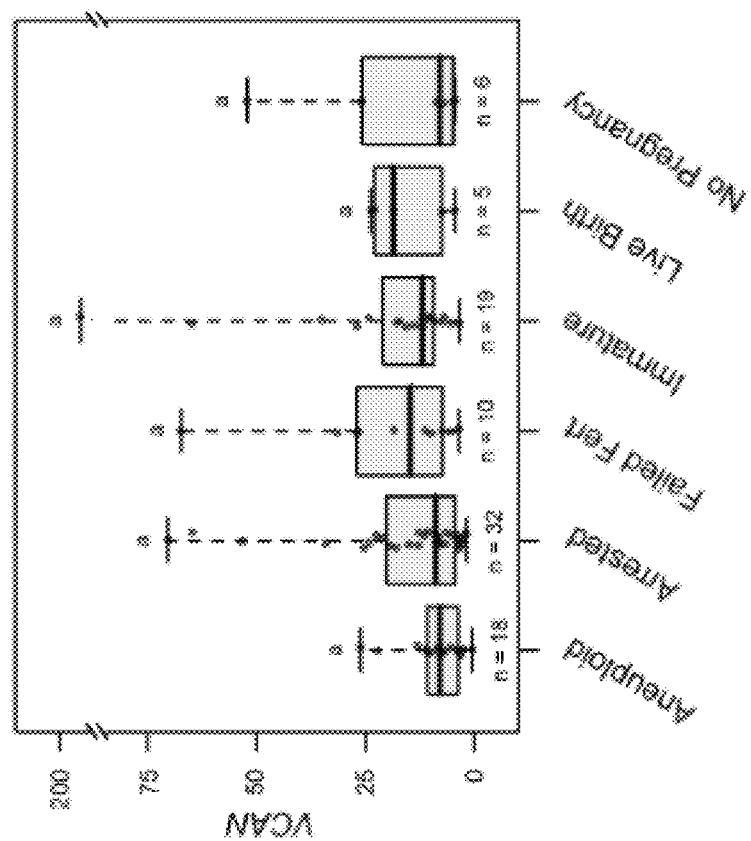
Figure 4O:
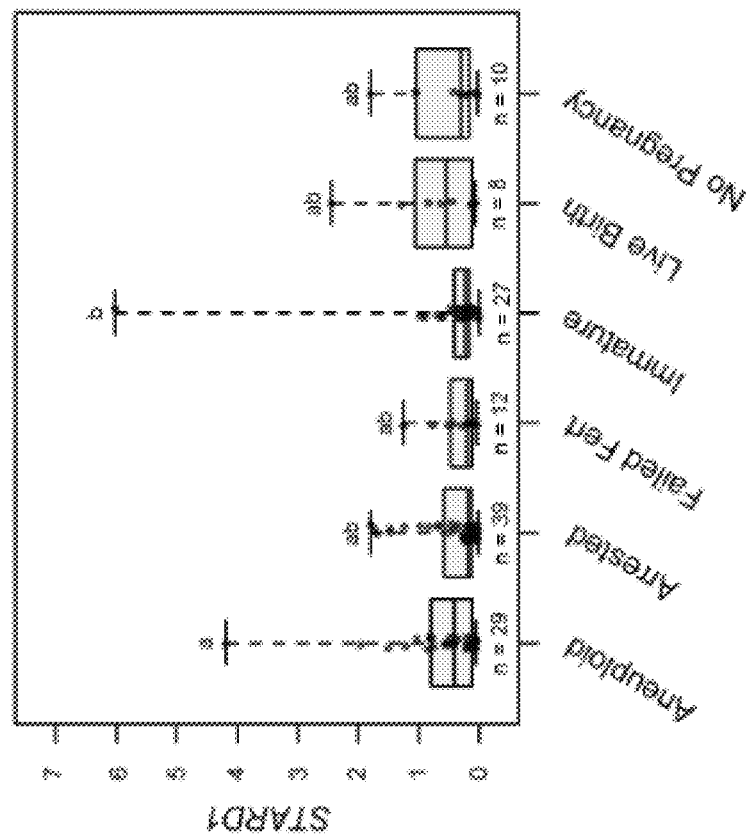

As another example, referring now to FIG. 4A, the figure illustrates the mRNA expression for several genes in cumulus cell masses harvested from oocytes, and the outcome for the corresponding oocytes. Generally, the mRNA expression for AREG resulting in a live birth outcome is lower than the mRNA expression for AREG in other outcomes (the median mRNA expression is lower than the median mRNA expression for other outcomes).

In certain implementations, selecting an oocyte for fertilization can include comparing the mRNA expression for two or more genes to the population value for each gene. For example, the mRNA expression for PAPPA can be compared to the population value for PAPPA (e.g., the population value can be determined as the lower quartile for live birth outcome according to FIG. 3A) and the mRNA expression for AREG can be compared to the population value for AREG (e.g., the population value can be determined as the upper quartile for live birth outcome according to FIG. 4A). Selecting the oocyte for fertilization can then include recommending fertilizing the oocyte associated with a cumulus cell mass displaying mRNA expression of PAPPA greater than the population value for PAPPA (e.g. the lower quartile or about 1.5) and the cumulus cell mass displaying mRNA expression of AREG less than the population value for AREG (e.g., the upper quartile or about 41).

Generally, determining the population value includes determining the mRNA expression of a gene from a population of cumulus cell masses isolated from a population of oocytes, fertilizing the population of oocytes, and tracking an outcome associated with mRNA expression of the gene. As described above, one possible outcome can include live birth, though other outcomes are possible and can be used to determine the population value. In some applications, such as in vitro fertilization (IFV), it may be desirable to know the oocyte associated with a cumulus cell mass having an mRNA expression for a gene that is associated with a live birth outcome. In other applications, such as research, it may be desirable to know the oocyte associated with a cumulus cell mass having an mRNA expression for a gene that is associated with failed fertilization. Thus, the population value does not necessarily need to be a set or static value and can be adjusted or determined based the application. For applications such as in vitro fertilization, the live birth outcome can be a desirable metric and aspects of the mRNA expression for oocytes having a live birth outcome may be used to determine the population value.

In certain embodiments, the population value and the mRNA expression for the gene can be normalized using the mRNA expression of a secondary gene (e.g., TATA-binding protein, TBP) and/or the maximum mRNA expression for the gene (e.g., dividing by the maximum mRNA expression to normalize the values between 0 and 1).

As an example, selecting the oocyte for fertilization can be based on determining the mRNA expression of AREG and/or HSD3B, normalizing the mRNA expression to values between 0 and 1, and comparing the normalized mRNA expression to the normalized population expression for the respective gene. Selecting the oocyte for fertilization can then favor or only select, an oocyte associated with a cumulus cell mass displaying one or more of the following: a normalized mRNA expression of AREG lower than 0.75, a normalized mRNA expression of HSD3B1 less than 0.75, or a normalized mRNA expression of both AREG and HSD3B1 less than 0.75. For example, an implementation can include selecting the oocyte associated with a cumulus cell mass displaying a normalized mRNA expression of AREG lower than 0.65, a normalized mRNA expression of HSD3B1 less than 0.65, or a normalized mRNA expression of both AREG and HSD3B1 less than 0.65. Another implementation can include selecting the oocyte associated with a cumulus cell mass displaying a normalized mRNA expression of AREG lower than 0.50, a normalized mRNA expression of HSD3B1 less than 0.50, or a normalized mRNA expression of both AREG and HSD3B1 less than 0.50. Further implementations may include different normalized population values for each gene or combinations of genes. For example, an implementation can include selecting the oocyte associated with a cumulus cell mass displaying a normalized mRNA expression of AREG lower than 0.75, a normalized mRNA expression of HSD3B1 less than 0.50, or a normalized mRNA expression of AREG and HSD3B1 less than 0.65.

In an example embodiment, selecting the oocyte for fertilization can include a recommendation. Example recommendations may be based on comparing the mRNA value to the population value. For instance, if the mRNA expression for AREG, HSD3B, or both is lower than the population value, a recommendation can include fertilizing the oocyte, recommending fertilizing the oocyte, implanting the fertilized oocyte, or recommending implanting the fertilized oocyte. If one or more of these conditions is not met, a recommendation can include not fertilizing the oocyte, harvesting cumulus cell masses from a different oocyte, or recommending not fertilizing the oocyte.

As another example, selecting the oocyte for fertilization can be based on determining the mRNA expression of LHCGR and/or PAPPA, normalizing the mRNA expression to values between 0 and 1, and comparing the normalized mRNA expression to the normalized population expression for the respective gene. Selecting the oocyte for fertilization can then favor or only select, an oocyte associated with a cumulus cell mass displaying one or more of the following: a normalized mRNA expression of LHCGR greater than 0.25, a normalized mRNA expression of PAPPA greater than 0.25, or a normalized mRNA expression of both LHCGR and PAPPA greater than 0.25. For example, an implementation can include selecting the oocyte associated with a cumulus cell mass displaying a normalized mRNA expression of LHCGR greater than 0.40, a normalized mRNA expression of PAPPA greater than 0.40, or a normalized mRNA expression of both LHCGR and PAPPA less than 0.40. Another implementation can include selecting the oocyte associated with a cumulus cell mass displaying a normalized mRNA expression of LHCGR greater than 0.50, a normalized mRNA expression of PAPPA greater than 0.50, or a normalized mRNA expression of both LHCGR and PAPPA greater than 0.50. Further implementations may include different normalized population values for each gene or combinations of genes. For example, an implementation can include selecting the oocyte associated with a cumulus cell mass displaying a normalized mRNA expression of LHCGR greater than 0.4, a normalized mRNA expression of PAPPA greater than 0.25, or a normalized mRNA expression of LHCGR and PAPPA greater than 0.30.

In an example embodiment, if the mRNA expression of LHCGR, PAPPA, or both is greater than the population value, a recommendation can include fertilizing the oocyte, recommending fertilizing the oocyte, implanting the fertilized oocyte, or recommending implanting the fertilized oocyte. If one or more of these conditions is not met, a recommendation can include not fertilizing the oocyte, harvesting a cumulus cell mass from a different oocyte, or recommending not fertilizing the oocyte.

The embodiments and methods disclosed can provide advantages in selecting an oocyte for maturation, an egg for fertilization, or an embryo for transfer by providing non-invasive protocols for measuring biomarkers that can aid in the prediction of live birth and/or successful fertilization. Additionally, cumulus cells play little to no role in the process of IVF since it is common practice in the course of normal IVF procedures, to discard the surrounding cumulus cells.

Being able to determine which oocytes are more likely to result in live birth can lead to fewer embryos needing to be implanted and/or fewer IVF cycles. As a result, patients can save money and time. Additionally, the methods disclosed are non-invasive and are used with cumulus cell masses, which are a byproduct of oocyte retrieval, whereas the pre-genetic testing requires removal of cells from the embryo itself. Since no cells are removed from the oocyte, ovum, or embryo, there is minimal risk of complications to the embryo. Thus, this disclosure can provide substantial benefits to both patients and IVF clinics by using information that would otherwise be discarded to reduce costs while also improving procedure outcomes.

With reference now to FIG. 1, embodiments of the disclosure include methods for performing selection oocytes including immature ovum, mature ovum, and fertilized oocytes. Generally, harvesting a cumulus cell mass from the cumulus-oocyte complex 101 can include: harvesting a cumulus cell mass from an immature ovum 101*a*, harvesting a cumulus cell mass from a mature ovum 101*b*, and/or harvesting a cumulus cell mass from a fertilized oocyte 101*c*. Embodiments of the disclosure can generally be practiced at any stage of oocyte (egg) maturity or at any stage of fertilization so long as a cumulus cell mass can be harvested from the egg or embryo. After harvesting a mRNA expression can be determined 102 for a gene expressed by the cumulus cell mass. Examples of different genes that can be used with embodiments of the disclosure include but are not limited to: AREG, CYP11A1, CYP19A1, FSHR, HSD3B, IGFBP5, INHBA, LHCGR, PGR, PGRMC1, PTGS2, ING1, and PAPPA. In an embodiment, the mRNA expression for at least two cumulus cell masses (the cumulus cell masses harvested from different oocytes or embryos) can be compared to determine the cumulus cell mass displaying a greater mRNA expression for the gene. For example, by comparing 103 the mRNA expression for the cumulus cell mass to the mRNA expression of a second cumulus cell mass for the same gene. In another embodiment, the mRNA expression can be compared to a population value determined at least in part using the outcomes from different oocytes or embryos. For example, by comparing 103 the mRNA expression for the cumulus cell mass to a population value correlating mRNA expression of the gene to a live birth outcome. Based at least in part on the comparison, a selection can be performed such as selecting the immature ovum 104*a*, selecting the mature ovum 104*b*, and selecting the fertilized oocyte 104*c*. At this point, the selected embryo or ovum may undergo a genetic test before proceeding with the IVF process.

Generally, the goal of IVF is a live birth with few or no complications for the patient undergoing the procedure. Thus, in certain implementations, selecting the immature ovum can further include administering a compound 105*a* to induce maturation or otherwise produce a mature ovum. For example, a compound such as luteinizing hormone and/or follicle-stimulating hormone can be administered. In some implementations, selecting the mature ovum can further include fertilizing 105*b* the selected mature ovum to produce an embryo. For example, spermatozoa can be introduced to the mature ovum. In some implementations, selecting the fertilized oocyte can further include implanting 105*c* the selected fertilized oocyte in a patient undergoing IVF. As shown by the dotted arrows, these additional steps may be implemented for each of the embodiments up to implanting the fertilized oocyte. At certain points in IVF, it may be useful to conduct genetic testing on the ovum or fertilized oocyte (i.e., embryo). Though not required in the embodiments shown in FIG. 1, genetic testing can be conducted in certain embodiments of the disclosure. For example, genetic testing can be conducted before harvesting 101 a cumulus cell mass from the cumulus-oocyte complex. Alternatively or additionally, genetic testing can be performed before, during, or after each of the steps shown in FIG. 1 including: 102, 103, 104*a*-104*c*, and 105*a*-105*c*.

EXAMPLE 1

Example 1 discusses various methods and procedures and provides exemplary embodiments that may be understood in conjunction with the Drawings and Description provided herein.

Methods

Patient Stimulation and CC Isolation

In total, 164 individual CC masses were harvested from their corresponding oocytes from 15 patients undergoing infertility treatment with PGT-A at Advanced Fertility and Reproductive Endocrinology Institute (Columbia, SC) from February 2015 through June 2016. This study involved the collection of the patient's demographics, cycle information (Supplemental Table 1), PGT-A results, live birth data, and CC mRNA expression levels. All patients underwent an antagonist protocol with rFSH (Gonal-f, EMD Serono). The patient's initial dose of medication was based upon age, BMI, and day 3 FSH levels. The patients' ovaries were stimulated until each patient had at least one follicle at 15 mm when a GnRH antagonist (Cetrotide, EMD-Serono or Ganirelix, EMD-Serono) was administered. When two follicles reached 18 mm or 50% of the follicles were ≥15 mm by ultrasound an ovulatory dose of human chorionic gonadotropin (hCG) (Pregnyl, EMD Serono) or Lupron (Leuprolide Acetate, Sandoz) was delivered. Thirty-six hours later patients underwent oocyte retrieval. Each CC mass was mechanically separated from its oocyte with 25-gauge needles and rinsed in medium (HTF-HEPES, Irvine) to remove blood, cell debris, and MGC. Each CC mass and its associated oocyte/embryo were kept separate throughout the entire process. The CC were transferred into RNase/DNase free tubes with 100 μL medium and snap frozen in liquid nitrogen within 30 minutes of the end of the retrieval. Samples were maintained in liquid nitrogen until they were transferred to dry ice and transported to the University of South Carolina School of Medicine for further processing. All samples were stored at −80° C. until subsequent RNA isolation.

Embryo Culture and Ploidy Assessment

Grafts Mature oocytes were inseminated via intracytoplasmic sperm injection. Fertilization was confirmed by the presence of two pronuclei and two polar bodies 16-18 h post insemination. Embryos were individually cultured in 20 μL drops (Global total, Global) under oil (Ovoil, Vitrolife) at 37° C., 6% $CO_2$, 5% $O_2$, 89% $N_2$ in a humidified atmosphere until day 5 or day 6 post retrieval. Embryo morphologies were assessed, and 3-7 trophectoderm cells were biopsied and sent to Igenomix (Miami, FL) for PGT-A using next-generation sequencing. The outcomes of all the injected oocytes were recorded to allow for retrospective analysis of the mRNA biomarkers selected in each corresponding CC mass. Frozen embryo transfers (FET) were performed with the highest quality euploid embryos using Gardner's blastocyst grading (36). Live birth outcomes were obtained from the patient's obstetrician including delivery dates, gender, and if there were any maternal or neonatal interventions or complications.

RNA Isolation and cDNA Synthesis

RNA was isolated from each CC mass using the Directzol MiniPrep Kit including the DNase treatment step according to manufacturer's instructions (Zymo Research, Irvine CA) with minor modifications. Samples were thawed in Trizol (Invitrogen) and allowed to equilibrate to room temperature and sit for 5 minutes. Five volumes of Trizol were used per 1 volume of CC suspension in 2.5 mL cryopreservation tubes. Following isolation, RNA concentration and purity were assessed at the wavelengths of 260 and 280 nm using a spectrophotometer with a 2 mm lid (NanoDrop 2000C, Thermo Scientific). Sample concentrations varied between 4 and 18 ng RNA/μl. Each sample was reverse transcribed into cDNA using the Bio-Rad iScript kit (Hercules CA) following manufacturer's instructions. The reverse transcription reaction was carried out in a thermocycler, for 5 minutes at 25° C., 30 min at 42° C., and 5 min at 85° C.

Quantitative Real-Time PCR

Primer sequences, concentrations, and annealing temperatures can be found in Supplemental Table 2. Primers were synthesized followed by cartridge purification (Life Technologies, Carlsbad, CA). PCR reactions were run with 2 or more wells per sample for 45 cycles and Ct values were averaged for further analyses. The reaction mixture was made with 2 μL of cDNA (6-27 ng starting RNA) from each sample, 300 nM upstream primer, 300 nM downstream primer, and 10 μL 2X SsoAdvanced Universal SYBR Green Supermix (Bio-Rad Laboratories, Hercules CA) and sterile PCR-grade water to a final volume to 20 μl per well. PCR-grade water was substituted for the cDNA as a negative control. PCR amplification was performed using the iCycler iQ Real-Time PCR Detection System (Bio-Rad). TATA-box binding protein (TBP) mRNA was used as an internal control (37). Correct sized amplicons were verified initially on agarose gels and by the presence of single melt-curve peaks. mRNA quantities and primer efficiencies were derived from a standard curve for each mRNA generated by serial dilutions of its purified amplicon. Target mRNA values were expressed relative to values of the TBP mRNA control.

Statistical Analysis

The mRNA levels were normalized using log 2 transformation. Principal Component Analysis (P. C. A.) was conducted to explore the mRNA level correlation patterns between the CC samples. The average mRNA levels were compared between different oocyte developmental outcomes using repeated measures analysis of variance (ANOVA) followed by Tukey's post hoc tests (adjusted p-values) for pairwise comparisons (38). Models were estimated to predict multiple dichotomous oocyte developmental outcomes using generalized linear mixed models (GLMM) fitted by maximum likelihood using the R package lme4 (39). The GLMMs included the normalized gene expressions as predictors and used patients' demographics (age and B. M. I.) as controlling factors. Unstructured correlation patterns were used in fitted GLMMs to capture the correlation among the repeated observations from same individual. Statistical significance in all analyses was determined at a 0.05 significance level. Statistical analysis was performed using the statistical software R 3.4.4.

Results

Results provided in the drawings and described herein are meant to be exemplary and are not intended to limit the methods and compositions to modifications or alternatives as would be understood by a person of ordinary skill in the field of endeavor.

In total, 164 CC were harvested from 15 patients undergoing infertility treatment with PGT-A. One or two embryos were transferred in utero in subsequent FETs once PGT-A results were obtained. In each of the cases where two embryos were transferred, one embryo of each gender was transferred. 163 of 164 CC samples (n=15 patients) analyzed contained a sufficient amount of RNA to detect the endogenous control, TBP. Due to limited starting sample volumes, not all samples were able to be tested for each biomarker and the variations in sample size due to this are noted on the accompanying figures. All fitted GLMMs included age and body mass index (BMI) as control variables in addition to the mRNA levels as main explanatory variables.

Biomarker mRNA Level Profiles of CC According to Ploidy Status

Figures 2G, 2H, 2I, 2J:
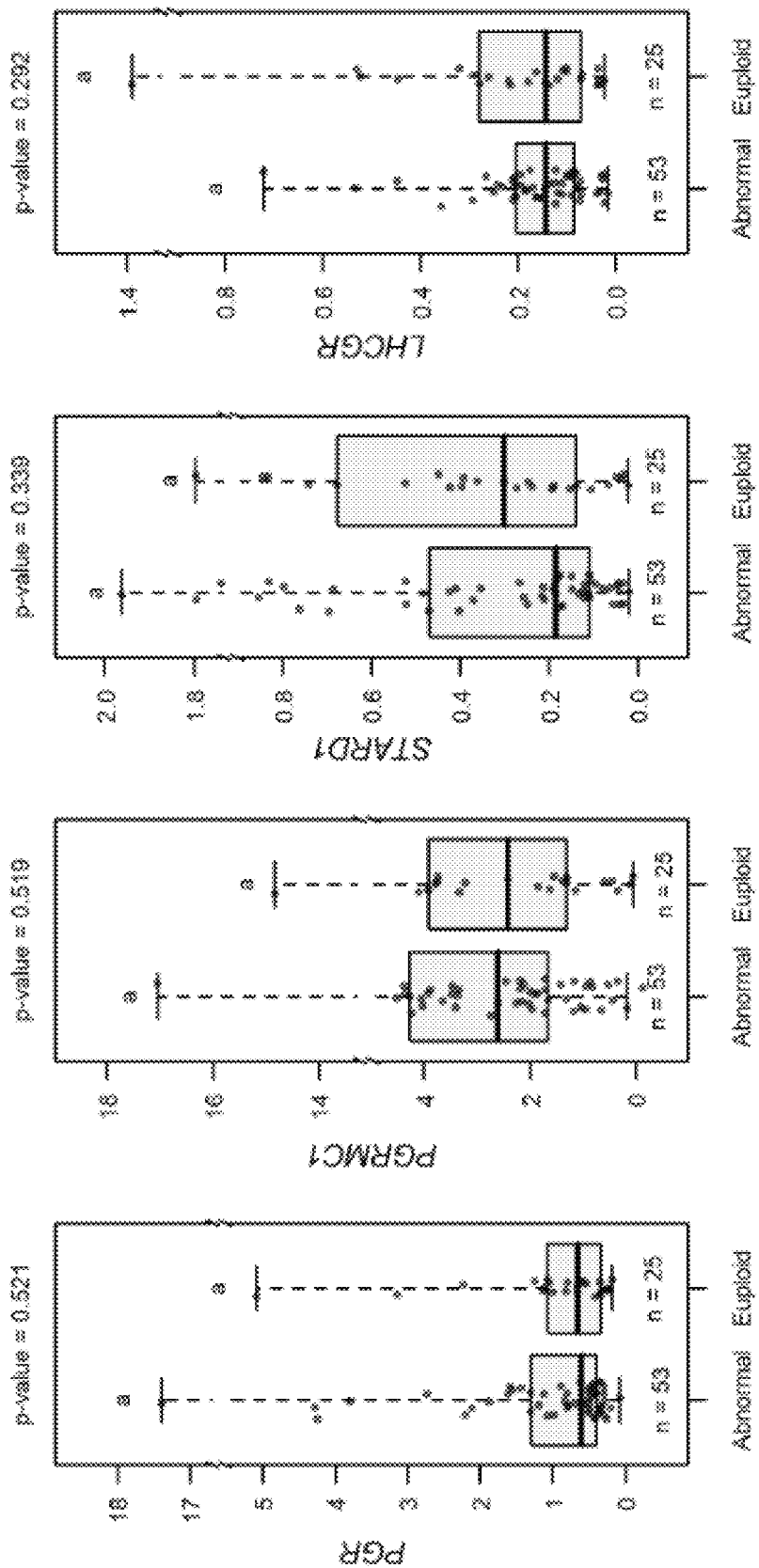

The best fitting model examining if CC biomarkers could predict if an oocyte would become a euploid embryo included 11 patients (n=78 CC masses) and the biomarkers CYP11A1, CYP19A1, HSD3B1, IGFBP5, PAPPA, PGR, PGRMC1, ING1, LHCGR, and STARD1. We found that lower HSD3B1 mRNA levels were significantly associated with euploid embryos (P<0.05) and higher ING1 mRNA levels trended toward being associated with euploid embryos (P<0.1) (FIGS. 2A-2C).

Biomarker mRNA Profiles of CC Evaluating Mature Oocyte Competence

Figure 3B:
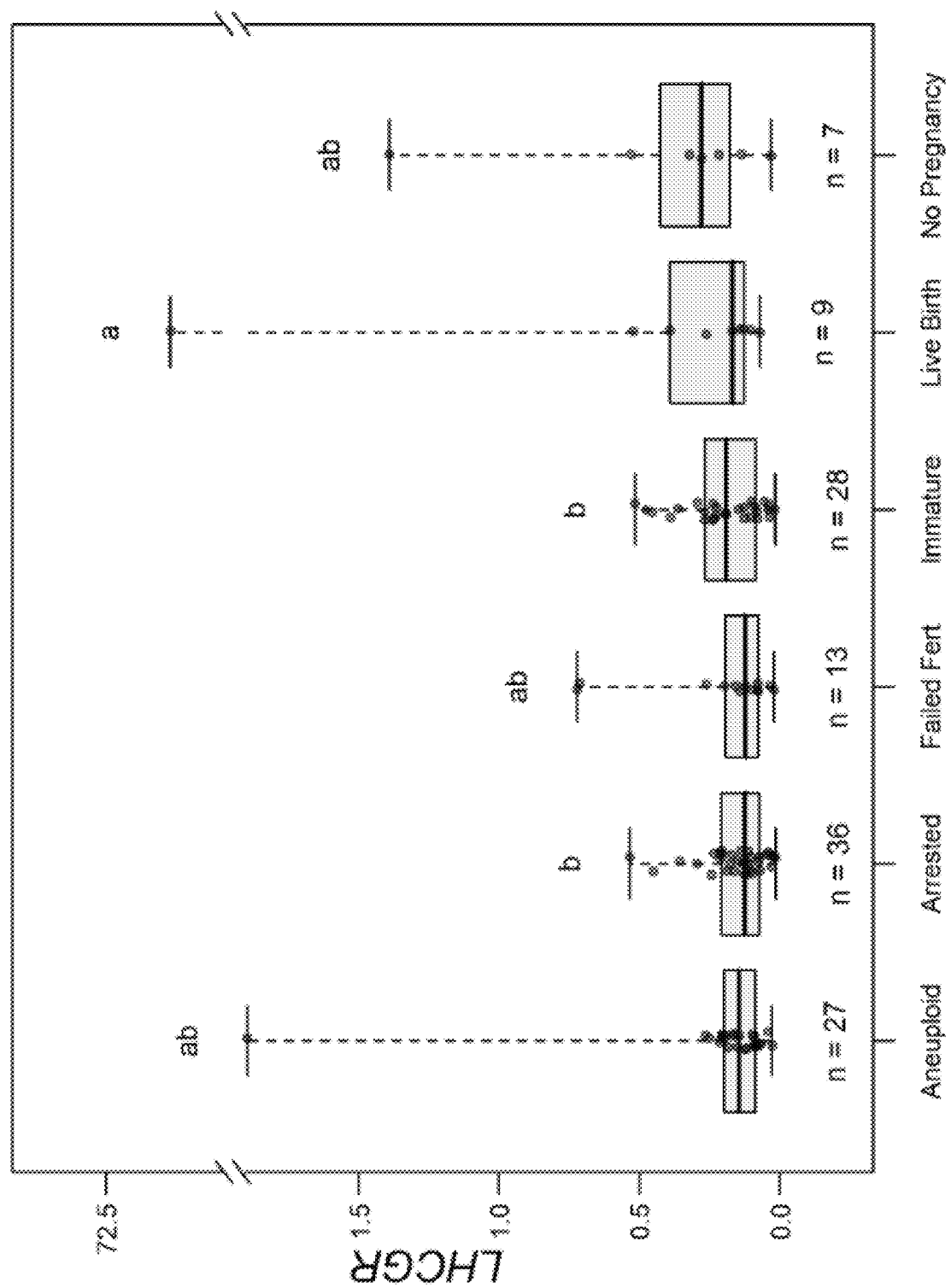

PAPPA mRNA levels significantly increased in aneuploid embryos and embryos that led to a live birth compared to immature oocytes (P<0.05). LHCGR mRNA levels significantly increased in embryos leading to a live birth compared to immature oocytes (P<0.05) (FIGS. 3A-3B). The other biomarkers showed no statistical differences between groups (FIGS. 4A-4D).

Biomarker mRNA Level Profiles of CC According to Live Birth Outcomes

Figure 5A:
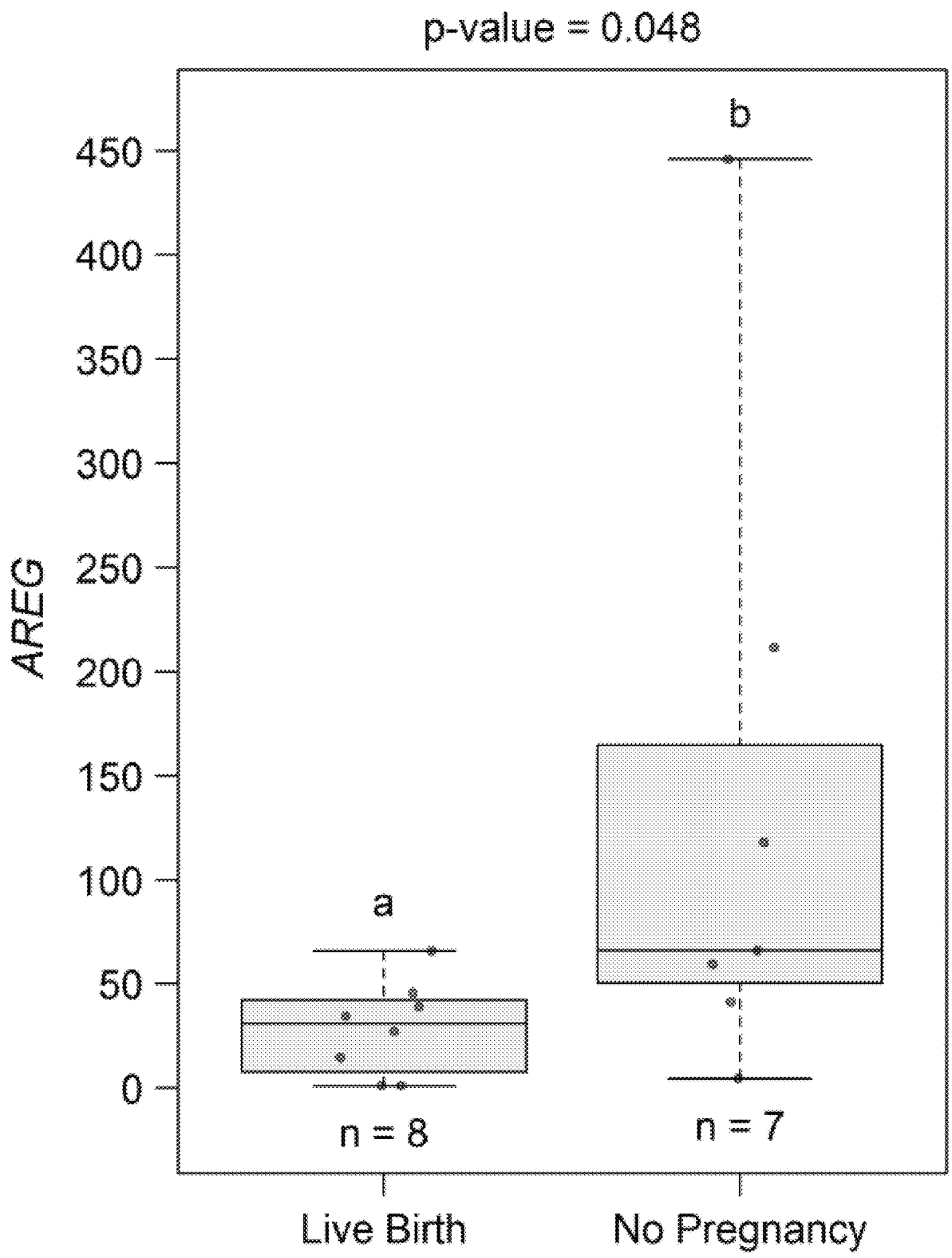
FIGS. 5A-5B illustrate example data for live birth and no pregnancy populations.
Figure 5B:
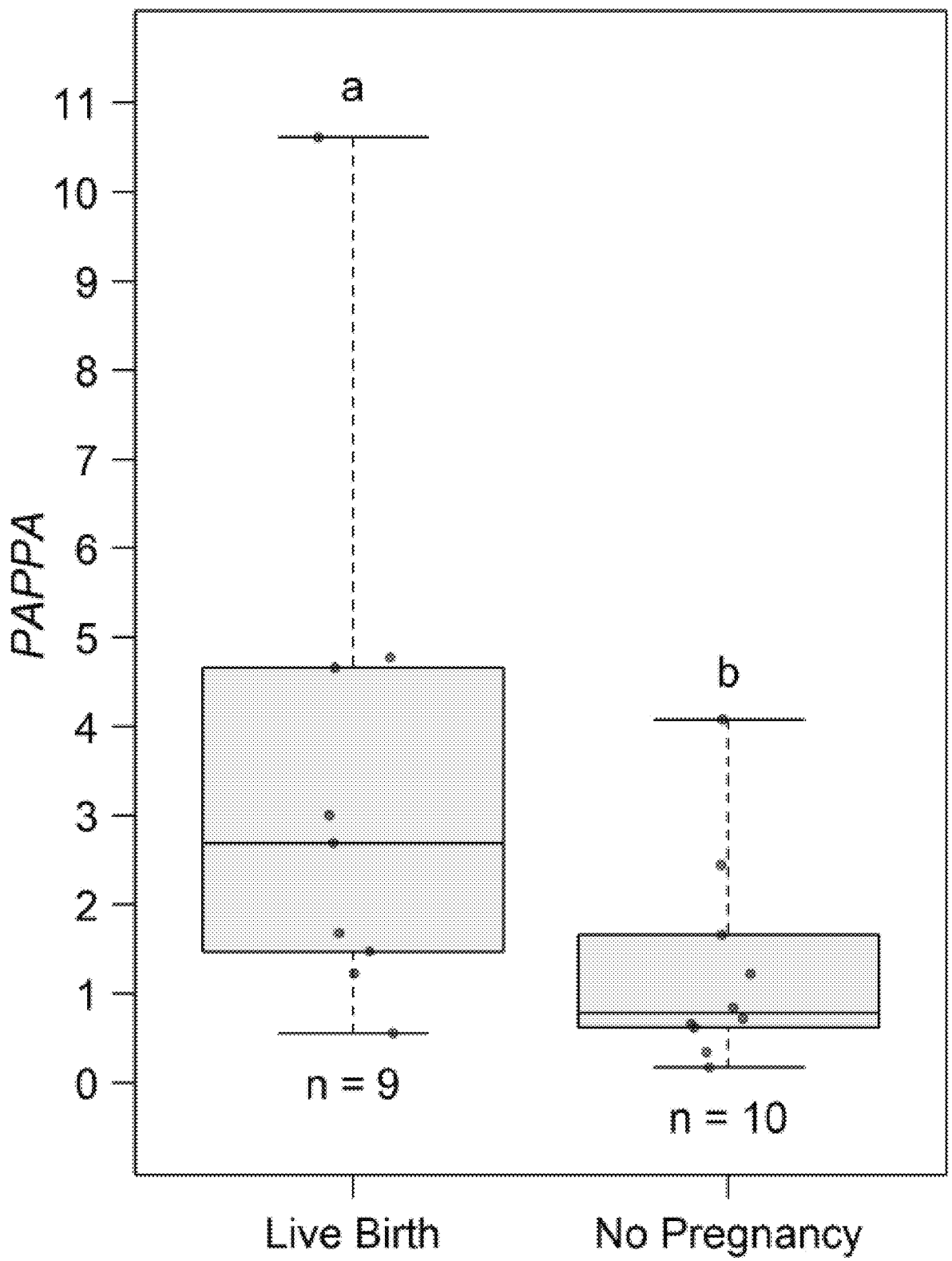
Figures 6A, 6B, 6C, 6D:
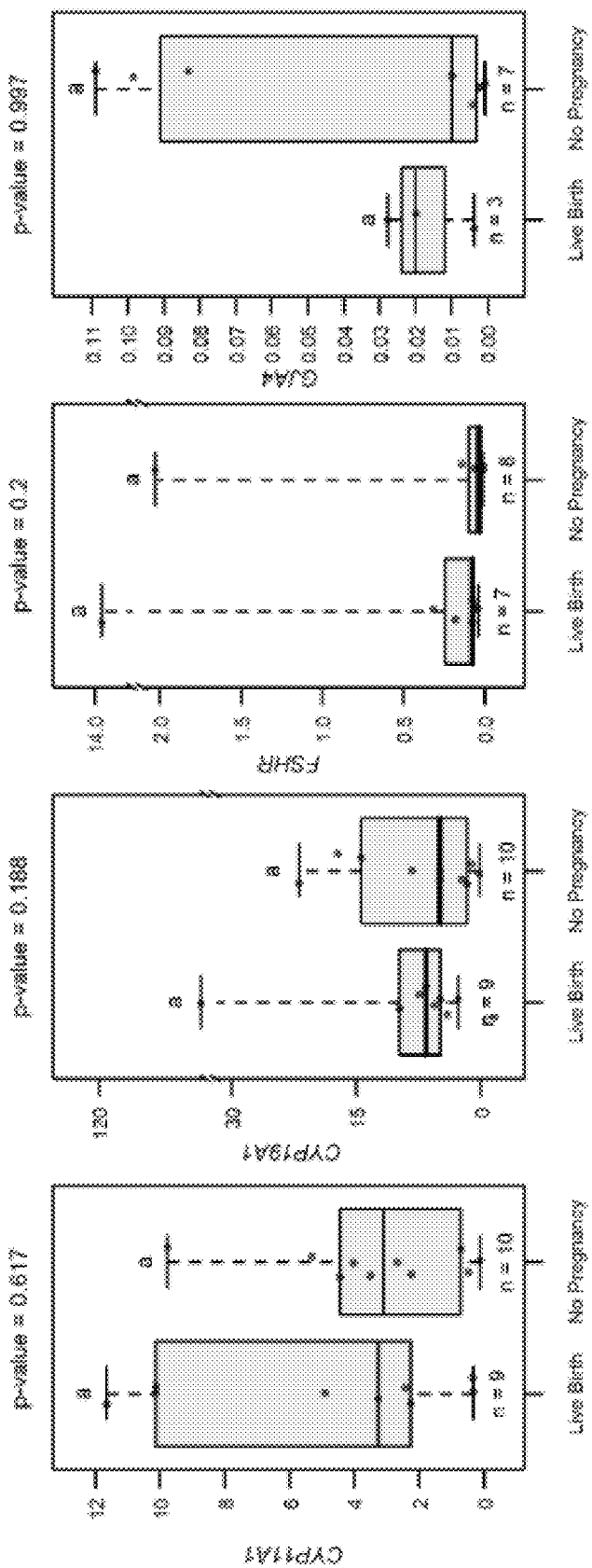
FIGS. 6A-6P further illustrate example data for live birth and no pregnancy populations.
Figures 6E, 6F, 6G, 6H:
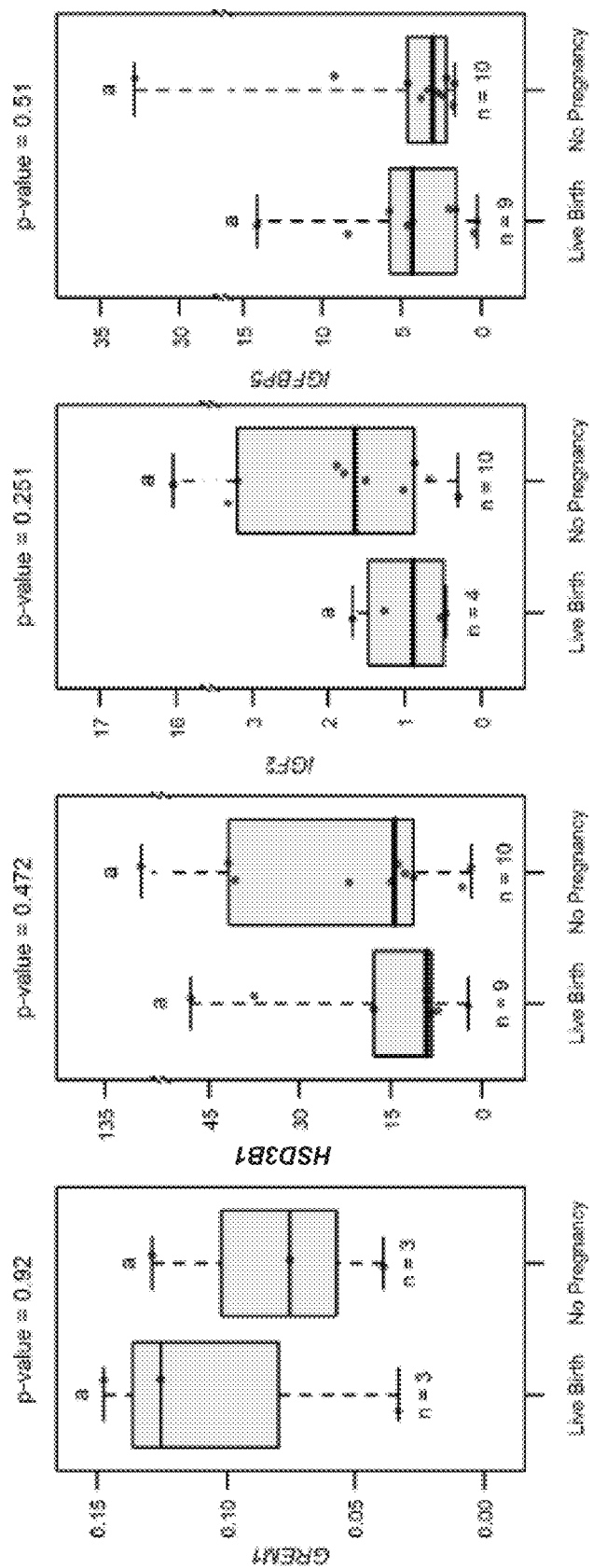
Figures 6I, 6J, 6K, 6L:
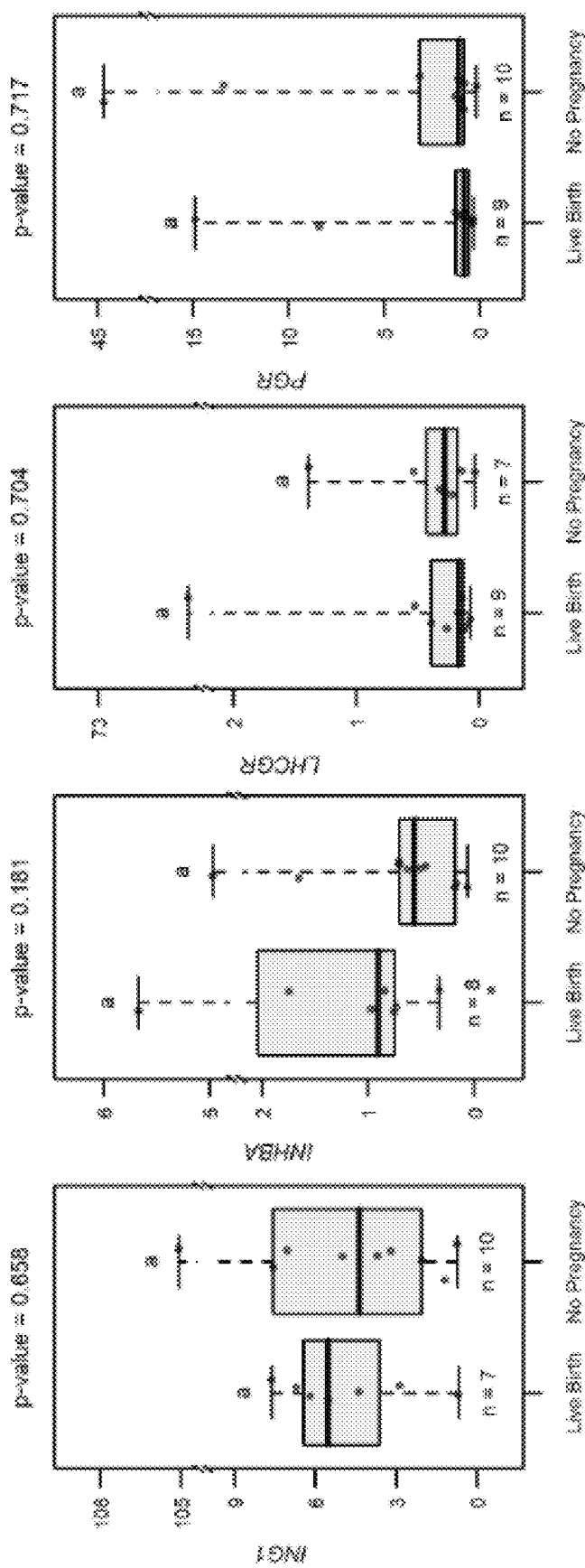
Figures 6M, 6N, 6O, 6P:
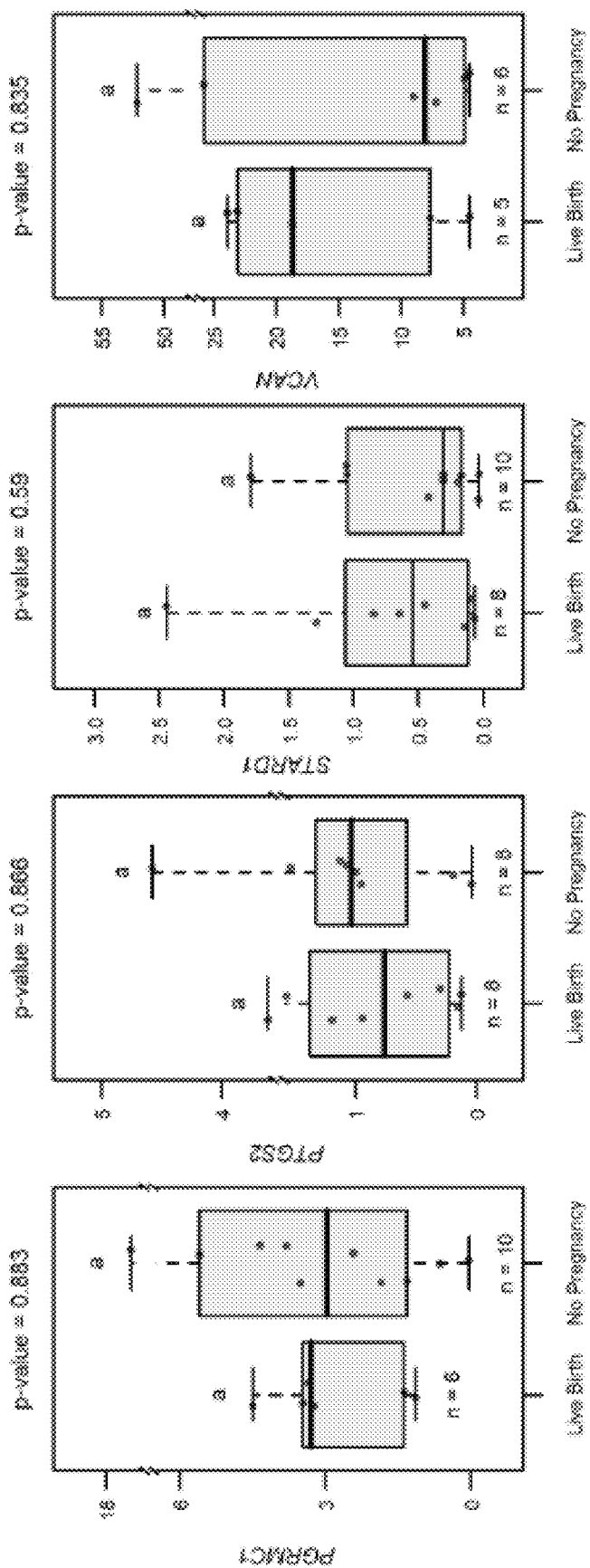
Figure 7A:
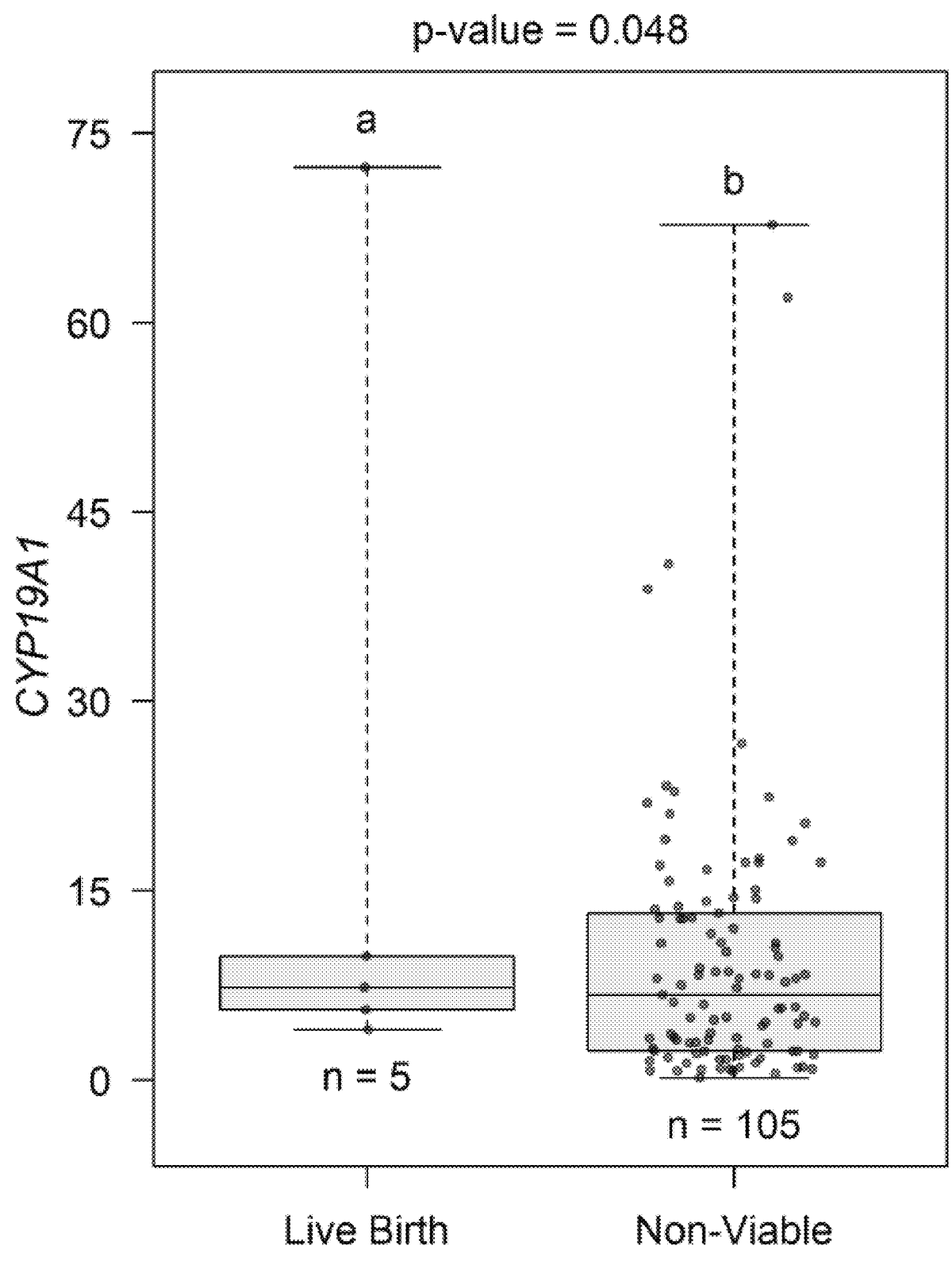
FIGS. 7A-7B illustrate example data for live birth and non-viable populations (cumulus cells from oocytes not able to yield a live birth).
Figure 7B:
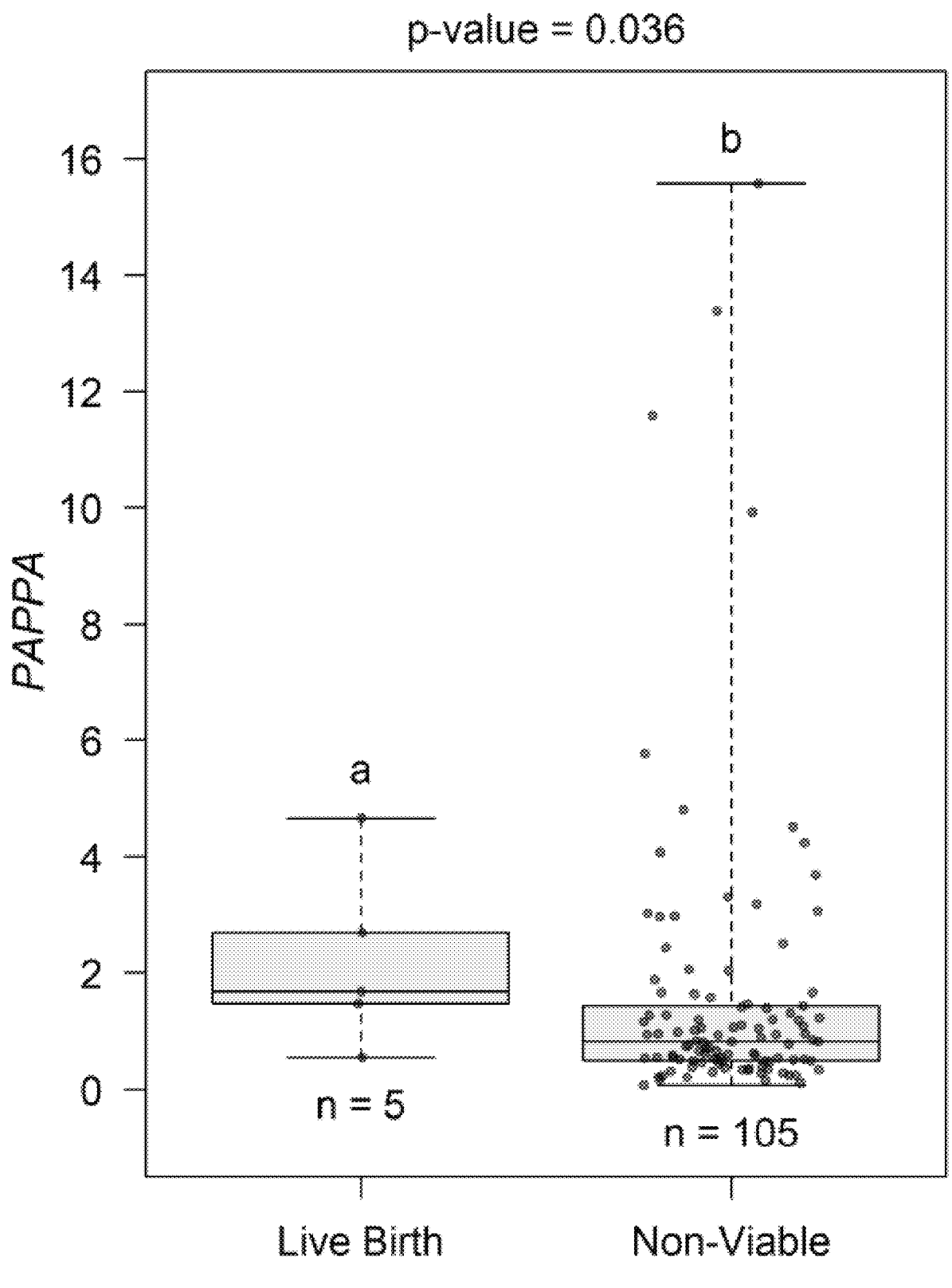
Figures 8A, 8B:
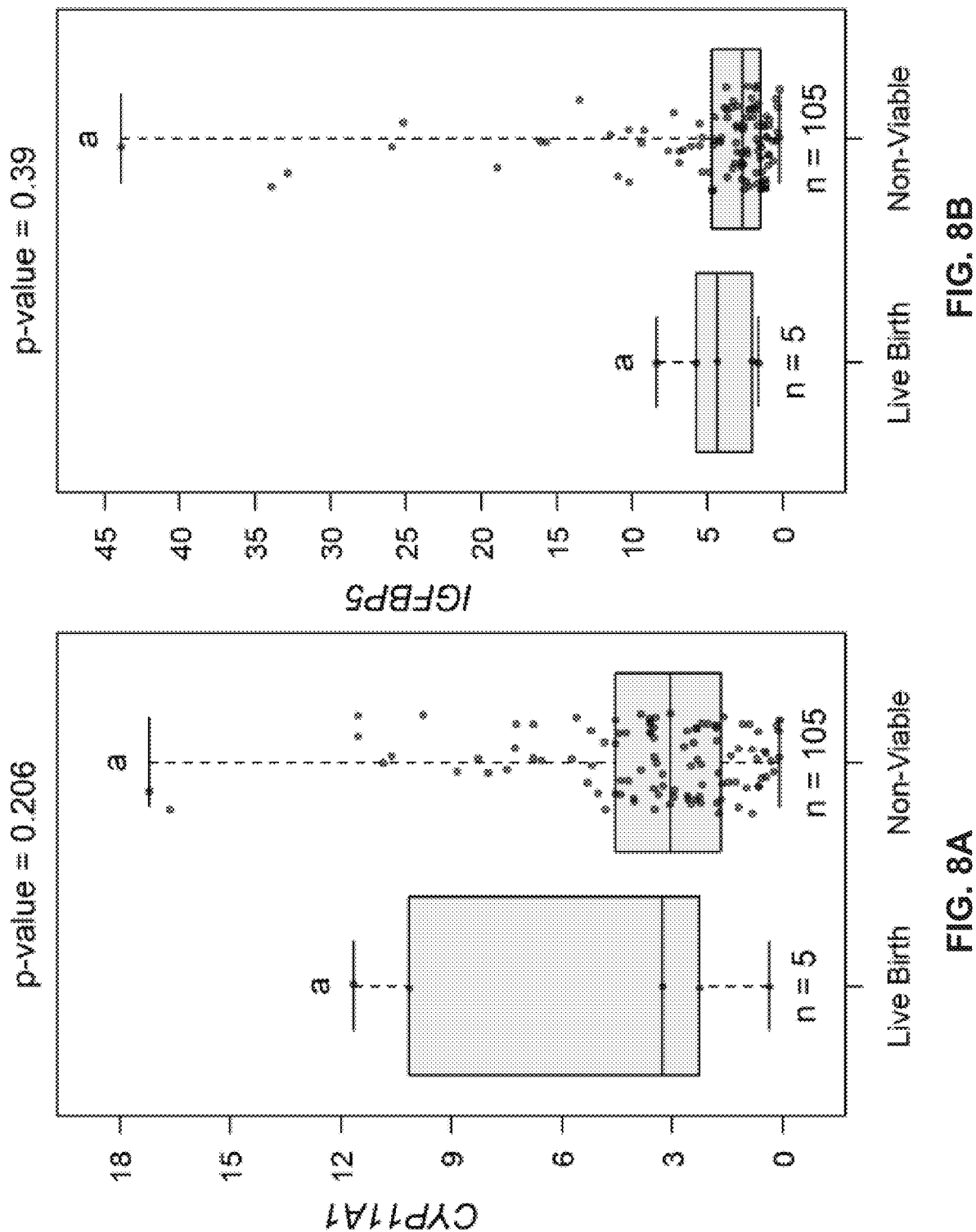
FIGS. 8A-8D further illustrate example data for live birth and non-viable populations.
Figures 8C, 8D:
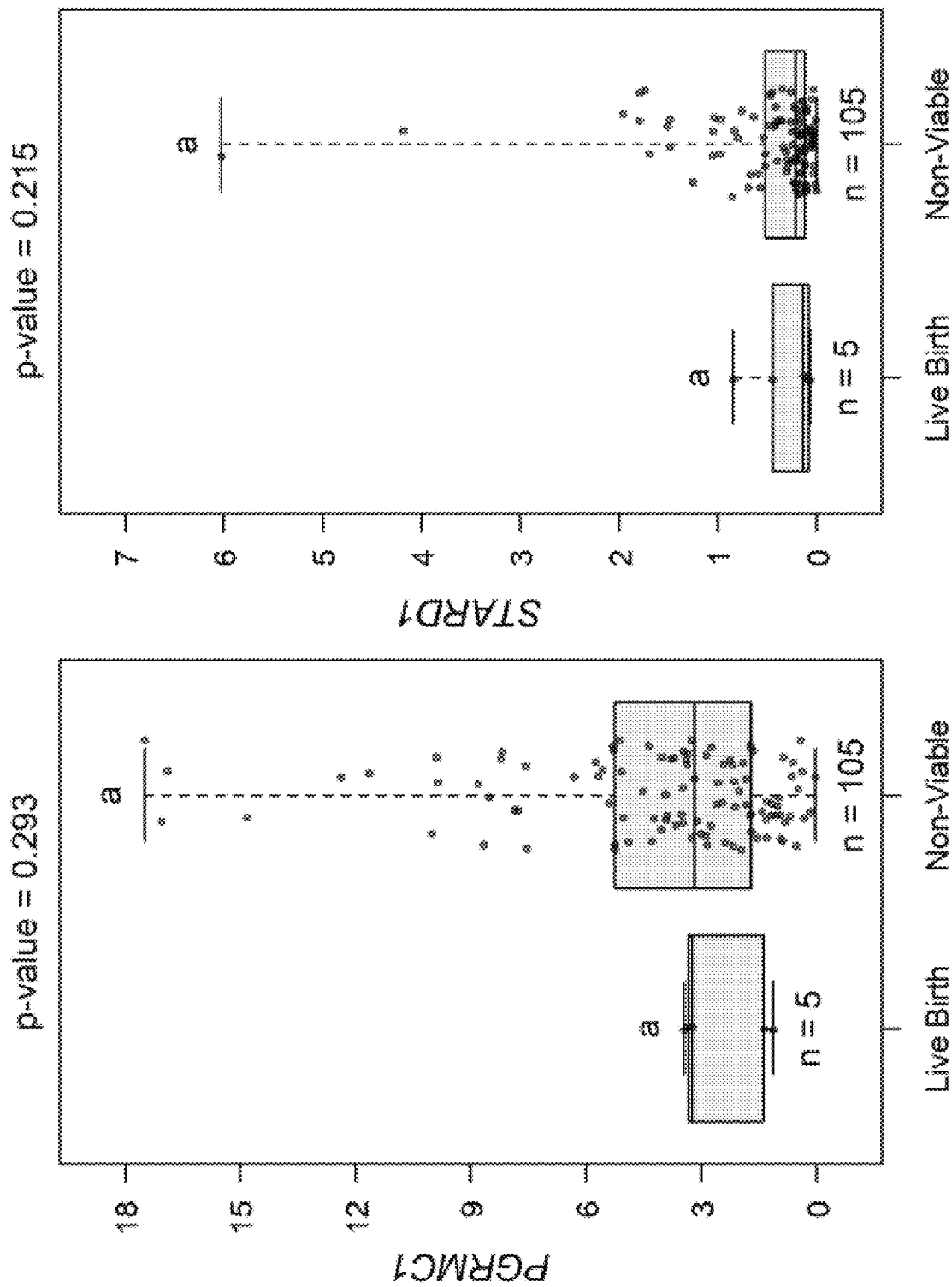

We examined whether the biomarker profiles were different for embryos that would produce viable pregnancies. Embryos from all 15 patients (n=19 CC masses) were assessed for mean mRNA level differences between those transferred embryos that resulted in a live birth and those that did not form a pregnancy. AREG mRNA levels were significantly decreased in CC from oocytes that resulted in live births (n=8 from 8 patients) compared to no pregnancy group (n=7 from 5 patients) (P<0.05). PAPPA mRNA levels were significantly increased in CC from embryos that resulted in live births (n=9 from 8 patients) than no pregnancy (n=10 from 7 patients) (P<0.05) (FIGS. 5A-5B). The other biomarkers showed no statistical differences between groups (FIGS. 6A-6B). To identify mRNA biomarkers capable of identifying euploid embryos producing a live birth, the best fitting model included 110 CC samples from 14 patients and included the biomarkers CYP11A, CYP19A1, IGFBP5, PAPPA, PGRMC1, and STARD1 (FIGS. 7A-7B). As revealed in the fitted model higher CYP19A1 and PAPPA mRNA levels (P<0.05) significantly increased the odds of an embryo resulting in a live birth (OR=4.397, 95% CI: 1.011, 19.125 and OR=4.574, 95% CI: 1.103, 18.951, respectively). The other biomarkers did not contribute statistically significant differences to predict live births (FIGS. 8A-8B).

The invention claimed is:

1. A method for performing oocyte selection comprising:
obtaining at least two cumulus-oocyte complexes from a donor;
harvesting a cumulus cell mass from each of the at least two cumulus-oocyte complexes, each cumulus cell mass associated with a corresponding oocyte from which the cumulus cell mass was harvested;
measuring an mRNA expression level of each gene of a set of genes from each cumulus cell mass, wherein the set of genes includes amphiregulin (AREG), hydroxy-delta-5-steroid dehydrogenase, 3 beta- and steroid delta-isomerase 1 (HSD3B1), luteinizing hormone/choriogonadotropin receptor (LHCGR), and Pappalysin 1 (PAPPA);
comparing the mRNA expression for each of the genes from at least two cumulus cell masses, each of the at least two cumulus cell masses harvested from different oocytes;
selecting the corresponding oocyte associated with one of the at least two cumulus cell masses based on the comparing of the mRNA expression for each of the genes, wherein the corresponding oocyte comprises a euploid oocyte;
wherein a relative decrease of mRNA expression level of AREG and/or HSD3B1 in the cumulus cell mass from the corresponding euploid oocyte compared to another cumulus cell mass from the corresponding euploid oocyte is indicative of a live birth outcome, or
wherein a relative increase of mRNA expression level of PAPPA and/or LHCGR in the cumulus cell mass from the corresponding euploid oocyte compared to another cumulus cell mass from the corresponding euploid oocyte is indicative of a live birth outcome;
fertilizing the selected oocyte in vitro to form an embryo; and
implanting the embryo in a patient.

2. The method of claim 1, wherein the step of comparing the mRNA expression comprises:
categorizing the mRNA expression for at least two cumulus cell masses based on a statistic determined using the mRNA expression, the statistic including one or more from the group comprising: a minimum, a maximum, a percentile, a mean, a median, a mode, and a probability.

3. The method of claim 1, wherein the donor is the same donor for each oocyte.

4. The method of claim 1, further comprising running genetic testing on the fertilized oocyte.

5. The method of claim 1, further comprising running genetic testing on the selected oocyte.

6. The method of claim 1, wherein selecting the corresponding oocyte comprises:
comparing the mRNA expression of AREG for at least two cumulus cell masses, and selecting the corresponding oocyte associated with the cumulus cell mass having a lower mRNA expression of AREG based on a threshold.

7. The method of claim 6, wherein the threshold is calculated from a percentile mRNA expression of AREG for each of at least two cumulus cell masses.

8. The method of claim 1, wherein selecting the corresponding oocyte comprises:
comparing the mRNA expression of HSD3B1 for at least two cumulus cell masses, and
selecting the corresponding oocyte associated with the cumulus cell mass having a lower mRNA expression of HSD3B1 based on a threshold.

9. The method of claim 1, wherein selecting the corresponding oocyte comprises:
comparing the mRNA expression of AREG for each of at least two cumulus cell masses;
comparing the mRNA expression of HSD3B1 for each of at least two cumulus cell masses; and
selecting the corresponding oocyte associated with the cumulus cell mass having a lower mRNA expression of AREG and HSD3B1.

10. The method of claim 1, wherein selecting the corresponding oocyte comprises:
comparing the mRNA expression of LHCGR for at least two cumulus cell masses, and
selecting the corresponding oocyte associated with the cumulus cell mass having a higher mRNA expression of LHCGR.

11. The method of claim 1, wherein selecting the corresponding oocyte comprises:

comparing the mRNA expression of PAPPA for at least two cumulus cell masses, and
selecting the corresponding oocyte associated with the cumulus cell mass having a higher mRNA expression of PAPPA.

12. The method of claim 1, wherein selecting the corresponding oocyte comprises:
comparing the mRNA expression of LHCGR for at least two cumulus cell masses;
comparing the mRNA expression of PAPPA for at least two cumulus cell masses; and
selecting the corresponding oocyte associated with the cumulus cell mass having a higher mRNA expression of LHCGR and PAPPA.

13. A method for selecting an oocyte for fertilization comprising:
harvesting a cumulus cell mass from an oocyte;
measuring an mRNA expression level of each gene of a set of a genes from the cumulus cell mass, wherein the set of genes includes amphiregulin (AREG), hydroxy-delta-5-steroid dehydrogenase, 3 beta- and steroid delta-isomerase 1 (HSD3B1), luteinizing hormone/choriogonadotropin receptor (LHCGR), and Pappalysin 1 (PAPPA);
comparing the mRNA expression of each gene to a population value;
selecting the oocyte for fertilization based on the comparison to the population value,
wherein a relative decrease of mRNA expression level of AREG and/or HSD3B1 in the cumulus cell mass from the corresponding euploid oocyte compared to another cumulus cell mass from the corresponding euploid oocyte is indicative of a live birth outcome, or
wherein a relative increase of mRNA expression level of PAPPA and/or LHCGR in the cumulus cell mass from the corresponding euploid oocyte compared to another cumulus cell mass from the corresponding euploid oocyte is indicative of a live birth outcome;
fertilizing the selected oocyte in vitro to form an embryo; and
implanting the embryo in a patient.

14. The method of claim 13, further comprising determining a normalized mRNA expression using an mRNA expression for a secondary gene.

15. The method of claim 13, wherein the step of comparing the mRNA expression level of each gene to the population value comprises:
determining the mRNA expression of the gene from a population of cumulus cell masses isolated from a population of oocytes;
fertilizing the population of oocytes and tracking an outcome;
associating the outcome to the mRNA expression of the gene.

16. The method of claim 13, wherein selecting the oocyte for fertilization comprises:
comparing the mRNA expression of LHCGR, PAPPA, or both to the population value for the same and
recommending fertilizing the oocyte using a test including:
if the mRNA expression is higher than the population value:
fertilizing the oocyte or recommending fertilizing the oocyte else:
recommending to not fertilize the oocyte.

* * * * *